(12) United States Patent
Gurewich

(10) Patent No.: US 10,081,673 B2
(45) Date of Patent: Sep. 25, 2018

(54) COMPOSITIONS AND METHODS FOR TREATING ANGIOGENESIS-RELATED DISORDERS

(71) Applicant: FFE THERAPEUTICS LLC, Cambridge, MA (US)

(72) Inventor: Victor Gurewich, Cambridge, MA (US)

(73) Assignee: FFE Therapeutics LLC, Cambridge, MA (US)

( * ) Notice: Subject to any disclaimer, the term of this patent is extended or adjusted under 35 U.S.C. 154(b) by 66 days.

(21) Appl. No.: 14/775,261

(22) PCT Filed: Mar. 13, 2014

(86) PCT No.: PCT/US2014/026675
§ 371 (c)(1),
(2) Date: Sep. 11, 2015

(87) PCT Pub. No.: WO2014/151917
PCT Pub. Date: Sep. 25, 2014

(65) Prior Publication Data
US 2016/0024194 A1    Jan. 28, 2016

Related U.S. Application Data

(60) Provisional application No. 61/785,345, filed on Mar. 14, 2013.

(51) Int. Cl.
| | | |
|---|---|---|
| *A61K 39/395* | (2006.01) | |
| *C07K 16/00* | (2006.01) | |
| *C07K 16/18* | (2006.01) | |
| *C07K 16/36* | (2006.01) | |
| *A61K 45/06* | (2006.01) | |
| *A61K 39/00* | (2006.01) | |

(52) U.S. Cl.
CPC .......... *C07K 16/18* (2013.01); *A61K 39/3955* (2013.01); *A61K 45/06* (2013.01); *C07K 16/36* (2013.01); *A61K 2039/505* (2013.01); *C07K 2317/21* (2013.01); *C07K 2317/24* (2013.01); *C07K 2317/33* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 4,851,334 A | * | 7/1989 | Kudryk | A61M 1/3687 210/646 |
| 5,599,678 A | * | 2/1997 | Kraus | C07K 14/75 435/13 |
| 5,654,403 A | * | 8/1997 | Smith | A61K 39/39591 424/133.1 |
| 2002/0182708 A1 | | 12/2002 | Cali et al. | |
| 2013/0164387 A9 | * | 6/2013 | Montero | A61K 31/702 424/649 |

FOREIGN PATENT DOCUMENTS

| | | | |
|---|---|---|---|
| EP | 0 922 761 | * | 6/1999 |
| WO | WO91/06315 | | 5/1991 |
| WO | WO 1991/06315 | | 5/1991 |
| WO | WO00/75175 | | 12/2000 |
| WO | WO 2002/48181 | | 6/2002 |
| WO | WO07/024921 | | 3/2007 |

OTHER PUBLICATIONS

Raut, S and Gaffney. Evaluation of the fibrin binding profile of two anti-fibrin monoclonal antibodies. Thrombosis and Haemostasis (1996), 76(1), 56-64, Abstract only.*
El-Ayoubi et al. A fibrin antibody binding to fibronectin induces potent inhibition of Angiogenesis. Thromb Haemost. Jan. 2015;113(1):143-53. (Year: 2015).*
International Search Report and Written Opinion dated Jul. 7, 2014 in international application No. PCT/US2014/026675, 34 pgs.
European Search Report; EP 14769535.7; dated Oct. 14, 2016; 11 pages.
Stirk et al., "Locating the active site for angiogenesis and cell proliferation due to fibrin fragment E with a phage epitope display library," General Pharmacol., 2002, 35:261-267.
El-Ayoubi et al., "A fibrin antibody binding to fibronectin induces potent inhibition of angiogenesis," Thrombosis & Haemostasis, 2015, 113(1):143-153.
Bradbury et al., "Standardize antibodies used in research," Nature, 2015, 518(7537):27-29.
Schlager et al., "Complete Local Tumor Regression with Antibody to Fibrin Fragment E[1]," J. Immunol., 1975, 115(4):976-981.

* cited by examiner

*Primary Examiner* — Maher M Haddad
(74) *Attorney, Agent, or Firm* — Fish & Richardson P.C.

(57) ABSTRACT

Provided herein are anti-angiogenic monoclonal antibodies and antigen-binding antibody fragments that selectively and specifically bind to an epitope in both fibronectin and either fibrinogen or fibrin fragment E, compositions containing these antibodies and antibody fragments, and methods of using these antibodies and antibody fragments.

23 Claims, 15 Drawing Sheets

Specification includes a Sequence Listing.

```
caggtccaactgcagcagcctgggtctgtgctggtgaggccgggagcttcagtgaaactg
Q   V   Q   L   Q   Q   P   G   S   V   L   V   R   P   G   A   S   V   K   L tcctgcaaggcttctggctacaccttcaccagctactggatgcactgggcgaagcagagg      CDR-H1
S   C   K   A   S  |G   Y   T   F   T   S   Y   W   M   H|  W   A   K   Q   R cctggacaaggccttgagtggattggacagattcatcctattagtggtaatattaagtac      CDR-H2
P   G   Q   G   L   E   W   I   G  |Q   I   H   P   I   S   G   N   I   K|  Y aatgagaagttcaagggcaaggccacactgactgtagacacatctcccagcacagcctac
N   E   K   F   K   G|  K   A   T   L   T   V   D   T   S   P   S   T   A   Y gtggatctcagcagcctgacatctgaggactctgcggtctattactgtgcaagagatact      CDR-H3
V   D   L   S   S   L   T   S   E   D   S   A   V   Y   Y   C   A   R  |D   T tactatactaataacgatgctgtggactactgggtcaaggaacctcagtcaccgtctcc
Y   Y   T   N   N   D   A   V   D   Y|  W   G   Q   G   T   S   V   T   V   S tcag  (SEQ ID NO:1)
 S    (SEQ ID NO:2)
```

$V_H$ domain of the "6E7" antibody produced by hybridoma PTA-120972

FIG. 8A

```
gacattgtgatgacccagtctcacaaattcatgtccacatcagtaggagacagggtcagc
D   I   V   M   T   Q   S   H   K   F   M   S   T   S   V   G   D   R   V   S atcacctgcaaggccagtcaggatgtgggtagtgttgtagcctggtatcaacagaaacca      CDR-L1
I   T   C  |K   A   S   Q   D   V   G   S   V   V|  A   W   Y   Q   Q   K   P ggacaatctcctaaactactgatttactgggcatccacccggcatactggaatccctaat      CDR-L2
G   Q   S   P   K   L   L   I   Y  |W   A   S   T   R   H   T|  G   I   P   N cgcttcacaggcaggggatctgggacagatttcactctcaccattaccaatgtgcagtct
R   F   T   G   R   G   S   G   T   D   F   T   L   T   I   T   N   V   Q   S gaagacttggcagattatttctgtcagcaatatagcaactatcctctcacgttcggtgct      CDR-L3
E   D   L   A   D   Y   F   C  |Q   Q   Y   S   N   Y   P   L   T|  F   G   A gggaccaagctggagctgaaac   (SEQ ID NO:9)
G   T   K   L   E   L   K   (SEQ ID NO:10)
```

$V_L$ domain of the "6E7" antibody produced by hybridoma PTA-120972

FIG. 8B

```
caggtgcagctgagggagtcagaacctggcctggtggcgccctcacagagcctgtccatc
 Q  V  Q  L  R  E  S  E  P  G  L  V  A  P  S  Q  S  L  S  I acatgcactgtctctgggttctcattaaccagctatgctgtaagctgggttcgccagcca    CDR-H1
 T  C  T  V  S |G  F  S  L  T  S  Y  A  V  S| W  V  R  Q  P ccaggcaagggtctggagtggcttggagtaatatggactggtggaggcacaaattataat    CDR-H2
 P  G  K  G  L  E  W  L  G |V  I  W  T  G  G  G  T  N  Y  N| tcagctctcaaatccagactgagcatcagcagagacaactccaagaatcaagttttctta
|S  A  L  K  S| R  L  S  I  S  R  D  N  S  K  N  Q  V  F  L aaaatgaacagtctgcaaactgatgacacagccaggtactactgtgccagatatagtaac    CDR-H3
 K  M  N  S  L  Q  T  D  D  T  A  R  Y  Y  C  A  R |Y  S  N| ctttactatgctatggactactggggtcaaggaacctcagtcaccgtctcctcag (SEQ ID NO:17)
|L  Y  Y  A  M  D  Y| W  G  Q  G  T  S  V  T  V  S  S     (SEQ ID NO:18)
```

V$_H$ domain of the "7A2" antibody produced by hybridoma PTA-120970

FIG. 9A

```
gacattgtgatgacccagtctcaaaaattcatgtccacatcagtaggagagagggtcagc
 D  I  V  M  T  Q  S  Q  K  F  M  S  T  S  V  G  E  R  V  S atcacctgcaaggccagtcagaatgtaggtactaatgttgcctggtatcagcagaaagca   CDR-L1
 I  T  C |K  A  S  Q  N  V  G  T  N  V  A| W  Y  Q  Q  K  A gggcagtctcttgaactgctgatctatggggcatccaaccggcacactggagtccctgat   CDR-L2
 G  Q  S  L  E  L  L  I  Y |G  A  S  N  R  H  T| G  V  P  D cgcttcacaggcagtggatctgggacagatttcaccctcaccatcaccaatgtgcagtct
 R  F  T  G  S  G  S  G  T  D  F  T  L  T  I  T  N  V  Q  S gaagacatgacaaattatttctgtgaacaatataggagctatcctctgacgttcggtgga   CDR-L3
 E  D  M  T  N  Y  F  C |Q  Q  Y  R  S  Y  P  L  T| F  G  G ggcagcaagctggaaatcaaac   (SEQ ID NO:25)
 G  S  K  L  E  I  K      (SEQ ID NO:26)
```

V$_L$ domain of the "7A2" antibody produced by hybridoma PTA-120970

FIG. 9B

```
caggtgcagctgagggagtcagaacctggcctggtggcgccctcacggagcctgtccatc
 Q  V  Q  L  R  E  S  E  P  G  L  V  A  P  S  R  S  L  S  I
```

```
acatgcactgtctctgggttctcattaaccagctatgctgtaagctgggttcgccagcca      CDR-H1
 T  C  T  V  S │G  F  S  L  T  S  Y  A  V  S│ W  V  R  Q  P
```

```
ccaggcaagggtctggagtggcttggagtaatatggactggtggaggcacaaattataat      CDR-H2
 P  G  K  G  L  E  W  L  G │V  I  W  T  G  G  G  T  N  Y  N│
```

```
tcagctctcaaatccagactgagcatcagcaaagacaactccaagaatcaagttttctta
│S  A  L  K  S│ R  L  S  I  S  K  D  N  S  K  N  Q  V  F  L
```

```
aaaatgaacagtctgcaaactgatgacacagccaggtactactgtgccagatatagtaac     CDR-H3
 K  M  N  S  L  Q  T  D  D  T  A  R  Y  Y  C  A  R │Y  S  N│
```

```
ctttactatgctatggactactggggtcaaggaacctcagtcaccgtctcctcag(SEQ ID NO:33)
│L  Y  Y  A  M  D  Y│W  G  Q  G  T  S  V  T  V  S  S  (SEQ ID NO:34)
```

V$_H$ domain of the "7A8" antibody produced by hybridoma PTA-120971

FIG. 10A

```
gacattgtgatgacccagtctcaaaaattcatgtccacatcagtaggagagagggtcagc
 D  I  V  M  T  Q  S  Q  K  F  M  S  T  S  V  G  E  R  V  S
```

```
atcacctgcaaggccagtcagaatgtaggtactaatgttgcctggtatcagcagaaagca      CDR-L1
 I  T  C │K  A  S  Q  N  V  G  T  N  V  A│ W  Y  Q  Q  K  A
```

```
gggcagtctcttgaactgctgatctatggggcatccaaccggcacactggagtccctgat      CDR-L2
 G  Q  S  L  E  L  L  I  Y │G  A  S  N  R  H  T│ G  V  P  D
```

```
cgcttcacaggcagtggatctgggacagatttcaccctcaccatcaccaatgtgcagtct
 R  F  T  G  S  G  S  G  T  D  F  T  L  T  I  T  N  V  Q  S
```

```
gaagacatgacaaattatttctgtgaacaatataggagctatcctctgacgttcggtgga     CDR-L3
 E  D  M  T  N  Y  F  C │E  Q  Y  R  S  Y  P  L  T│ F  G  G
```

```
ggcagcaagctggaaatcaaac (SEQ ID NO:25)
 G  S  K  L  E  I  K   (SEQ ID NO:26)
```

V$_L$ domain of the "7A8" antibody produced by hybridoma PTA-120971

FIG. 10B

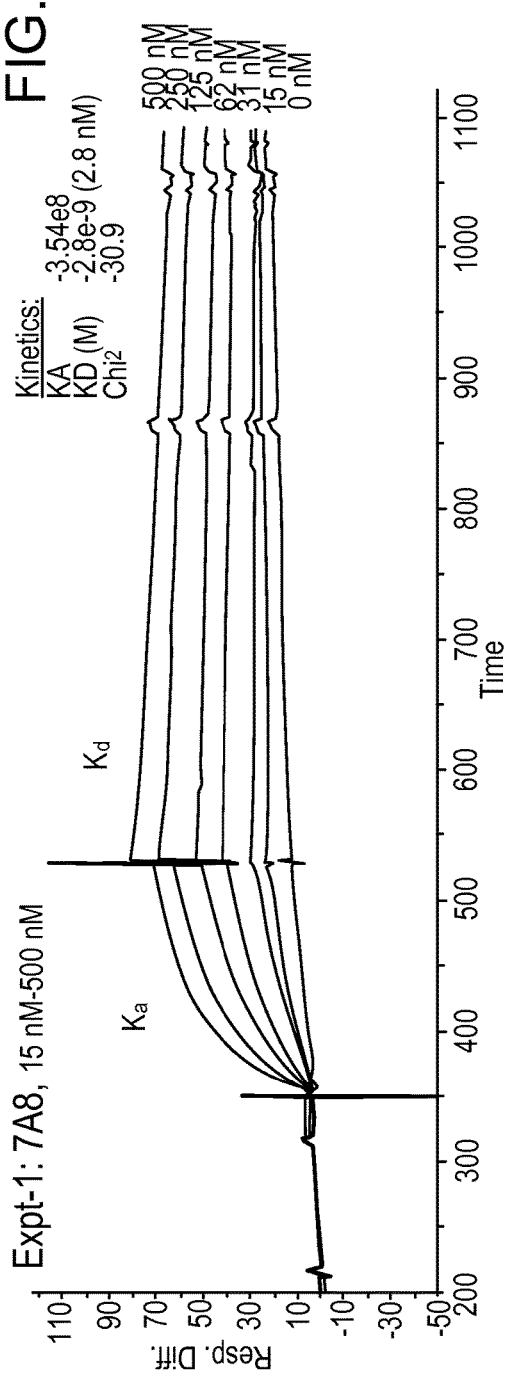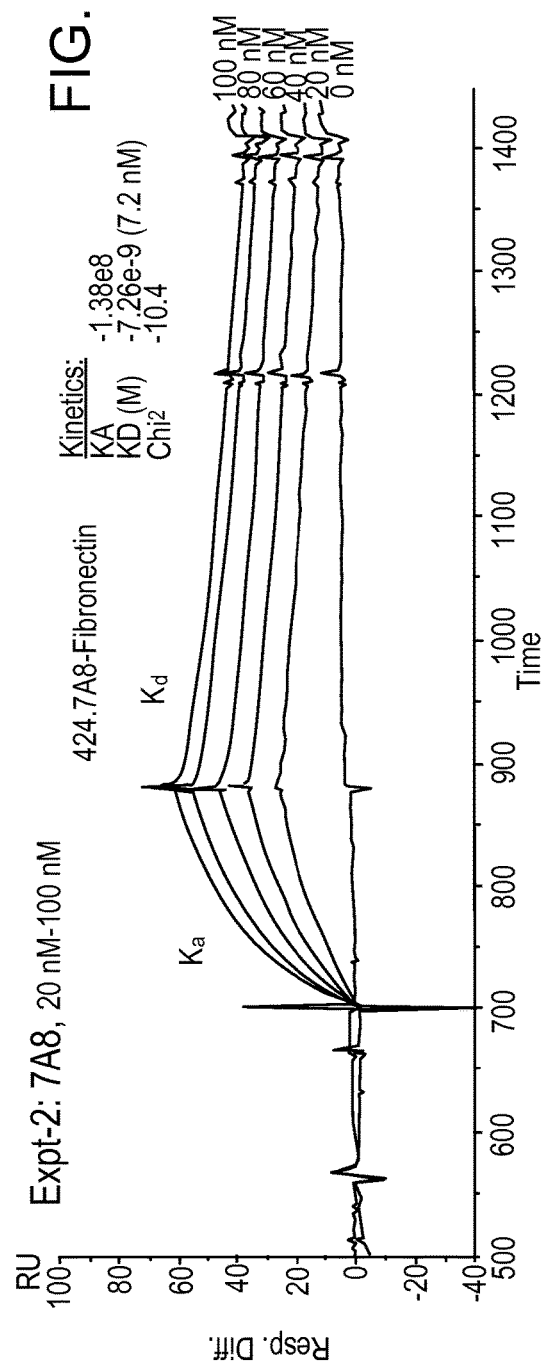

COMPOSITIONS AND METHODS FOR TREATING ANGIOGENESIS-RELATED DISORDERS

CROSS-REFERENCE TO RELATED APPLICATIONS

This application is a U.S. national stage application under 35 USC § 371 of International Application No. PCT/US2014/026675 filed on Mar. 13, 2014, which claims the benefit of U.S. Provisional Application Ser. No. 61/785,345, filed on Mar. 14, 2013, the entire contents of both of which are hereby incorporated by reference in their entireties.

TECHNICAL FIELD

This invention relates to compositions and methods for inhibiting angiogenesis and treating angiogenesis-related disorders.

BACKGROUND

During a normal life cycle, two types of blood vessels exist: the resting and quiescent fully developed blood vessels in adults, and the proliferating or developing new blood vessels that are found only in early development and reproduction, e.g., menstrual cycle and pregnancy. In contrast, angiogenesis, the proliferation and development of new blood vessels, occurs physiologically in wound healing and pathologically it is associated with processes like tumor growth and macular degeneration. Angiogenesis is a complex process involving many stages, including extracellular matrix remodeling, endothelial cell migration and proliferation, capillary differentiation, and anastomosis.

Angiogenesis can be a target for treating diseases characterized by abnormal neovascularization. The presence of extra blood vessels where there should be none affects the mechanical properties of a tissue, increasing the likelihood of failure. This is illustrated by wet macular degeneration in which the local expansion of blood vessels threatens macular vision. In addition, all detectable solid tumors (tumors over 2 mm in diameter) need angiogenesis to deliver oxygen and nutrients to actively proliferating tumor cells and remove cellular wastes. The level of vascularization in a tumor is also associated with metastasis of cancer cells.

SUMMARY

The present disclosure is based, at least in part, on the development of new monoclonal antibodies that selectively and specifically bind to both fibronectin and either fibrinogen or fibrin fragment E. These antibodies and antigen-binding fragments thereof are useful for inhibiting angiogenesis and for treating angiogenesis-related diseases, e.g., solid tumors and wet macular degeneration. Unlike other anti-angiogenic antibodies, these new antibodies do not inhibit growth factors, like vascular endothelial growth factor (VEGF), and do not inhibit cell proliferation. Provided herein are these antibodies and antigen-binding fragments thereof, compositions and kits containing these antibodies and antibody fragments, and various methods of using these antibodies and antigen-binding fragments.

In general, in one aspect the disclosure features isolated monoclonal antibodies or antigen-binding fragments thereof that are raised against fibrinogen and bind to both fibronectin and fibrinogen. In some embodiments, the new monoclonal antibodies or antigen-binding fragments bind to both human fibronectin and human fibrinogen.

In some embodiments, the new monoclonal antibodies or antigen-binding fragments bind to both fibronectin and fibrin fragment E. In some embodiments, the new monoclonal antibodies or antigen-binding fragments bind to both human fibronectin and human fibrin fragment E.

The new antibodies or antigen-binding fragments thereof have anti-angiogenic effects, but do not inhibit endothelial cell proliferation. In some embodiments, the new antibodies or antigen-binding fragments thereof are chimeric antibodies. In some embodiments, the new antibodies or antigen-binding fragments thereof are humanized. The antigen-binding fragments can be Fab fragments, F(ab')2 fragments, scFv fragments, or diabodies.

In another general aspect, the disclosure includes compositions that include at least one isolated monoclonal antibody or antigen-binding fragment disclosed herein.

In some embodiments, the compositions can include one or more complementary angiogenesis inhibitors. For example, the compositions can include any one or more of the angiogenesis inhibitors selected from the group consisting of, but not limited to, bevacizumab, sorafenib, sunitinib, pazopanib, axitinib, cabozantinib, regorafenib, vandetanib, temsirolimus, everolimus, lenalidomide, erlotinib, angiostatin, endostatin, tumstatin, canstatin, restin, and arresten. In some embodiments, the compositions can include one or more chemotherapeutic agents.

In yet another aspect, the disclosure includes methods of inhibiting angiogenesis and methods of treating angiogenesis-related disorder in a subject, e.g., a human, as well as uses of the compositions described herein to treat such angiogenesis-related disorders. The methods of inhibiting angiogenesis in a subject include administering to the subject an effective amount of one or more of the compositions disclosed herein. The methods of treating an angiogenesis-related disorder in a subject include first identifying a subject that has an angiogenesis-related disorder; and then administering to the subject an effective amount of a monoclonal antibody described herein, e.g., one that binds to both fibronectin and fibrinogen or one that binds to both fibronectin and fibrin fragment E. The monoclonal antibodies disclosed herein can be administered by various routes, e.g., intravenously, intradermally, subcutaneously, or orally.

In some embodiments, the new monoclonal antibodies disclosed herein are used to treat a solid tumor, for example, a sarcoma, a carcinoma, or a lymphoma. In some embodiments, the new monoclonal antibodies disclosed herein are used to treat wet macular degeneration. In such treatment methods, the new monoclonal antibodies disclosed herein can be used in combination with one or more chemotherapeutic agents and/or one or more angiogenesis inhibitors selected from the group consisting of, but not limited to, bevacizumab, sorafenib, sunitinib, pazopanib, axitinib, cabozantinib, regorafenib, vandetanib, temsirolimus, everolimus, lenalidomide, erlotinib, angiostatin, endostatin, tumstatin, canstatin, restin, or arresten.

Also provided are purified cells of the hybridomas deposited at the American Type Culture Collection (ATCC) and designated as PTA-120972, PTA-120970, or PTA-120971.

Disclosed herein are isolated monoclonal antibodies or antigen-binding fragments thereof that (1) bind to both human fibronectin and human fibrinogen, and (2) bind competitively with any one of the antibodies produced by the hybridoma deposited at the American Type Culture Collection (ATCC) and designated as PTA-120972, PTA-120970, or PTA-120971.

In some embodiments, the isolated monoclonal antibodies or antigen-binding fragments thereof (1) bind to both human fibronectin and human fibrinogen, and (2) recognize the same epitope as any one of the antibodies produced by the hybridoma deposited at the ATCC and designated as PTA-120972, PTA-120970, or PTA-120971.

In some embodiments, the isolated monoclonal antibodies or antigen-binding fragments thereof (1) bind to both human fibronectin and human fibrinogen, and (2) comprise the same heavy and light chain CDRs as the antibody produced by the hybridoma deposited at the ATCC and designated as any one of PTA-120972, PTA-120970, and PTA-120971. In some embodiments, the isolated monoclonal antibodies or antigen-binding fragments thereof comprise a heavy chain variable region that is at least 65% identical to SEQ ID NO:2 or 18, and a light chain variable region that is at least 65% identical to SEQ ID NO:10 or 26.

In some embodiments, the isolated monoclonal antibodies or antigen-binding fragments thereof (1) bind to both human fibronectin and human fibrinogen, and (2) comprise a heavy chain CDR1, a heavy chain CDR2, and a heavy chain CDR3. The heavy chain CDR1 can comprise the amino acid sequence of SEQ ID NO:4 or 20, or the amino acid sequence of SEQ ID NO:4 or 20 with a substitution at one, two, or three amino acid positions. The heavy chain CDR2 can comprise the amino acid sequence of SEQ ID NO:6 or 22, or the amino acid sequence of SEQ ID NO:6 or 22 with a substitution at one, two, or three amino acid positions. The heavy chain CDR3 can comprise the amino acid sequence of SEQ ID NO:8 or 24, or the amino acid sequence of SEQ ID NO:8 or 24 with a substitution at one, two, or three amino acid positions. In some embodiments, the isolated monoclonal antibodies or antigen-binding fragments can further include one or more of the following light chain CDRs: (1) a light chain CDR1 comprises the amino acid sequence of SEQ ID NO:12 or 28, or the amino acid sequence of SEQ ID NO:12 or 28 with a substitution at one, two, or three amino acid positions; (2) a light chain CDR2 comprises the amino acid sequence of SEQ ID NO:14 or 30, or the amino acid sequence of SEQ ID NO:14 or 30 with a substitution at one, two, or three amino acid positions; and (3) a light chain CDR3 comprises the amino acid sequence of SEQ ID NO:16 or 32, or the amino acid sequence of SEQ ID NO:16 or 32 with a substitution at one, two, or three amino acid positions.

In some embodiments, the isolated monoclonal antibodies or antigen-binding fragments thereof (1) bind to both human fibronectin and human fibrinogen, and (2) comprise a light chain CDR1, a light chain CDR2, and a light chain CDR3. The light chain CDR1 can comprise the amino acid sequence of SEQ ID NO:12 or 28, or the amino acid sequence of SEQ ID NO:12 or 28 with a substitution at one, two, or three amino acid positions. The light chain CDR2 can comprise the amino acid sequence of SEQ ID NO:14 or 30, or the amino acid sequence of SEQ ID NO:14 or 30 with a substitution at one, two, or three amino acid positions. The light chain CDR3 can comprise the amino acid sequence of SEQ ID NO:16 or 32, or the amino acid sequence of SEQ ID NO:16 or 32 with a substitution at one, two, or three amino acid positions.

In some embodiments, the isolated monoclonal antibodies or antigen-binding fragments can further include one or more of the following heavy chain CDRs: (1) a heavy chain CDR1 comprises the amino acid sequence of SEQ ID NO:4 or 20, or the amino acid sequence of SEQ ID NO:4 or 20 with a substitution at one, two, or three amino acid positions; (2) a heavy chain CDR2 comprises the amino acid sequence of SEQ ID NO:6 or 22, or the amino acid sequence of SEQ ID NO:6 or 22 with a substitution at one, two, or three amino acid positions; and (3) a heavy chain CDR3 comprises the amino acid sequence of SEQ ID NO:8 or 24, or the amino acid sequence of SEQ ID NO:8 or 24 with a substitution at one, two, or three amino acid positions.

In some embodiments, the one, two, or three amino acid substitutions are conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Conservative amino acid substitutions typically include substitutions within the same family.

In some embodiments, the isolated monoclonal antibodies or antigen-binding fragments thereof are a humanized or fully human antibody. For example, the monoclonal antibodies or antigen-binding fragments thereof can be a humanized or fully human version of the antibody produced by the hybridoma deposited at the ATCC and designated as any one of PTA-120972, PTA-120970, and PTA-120971.

In some embodiments, the antigen-binding fragments can be a Fab fragment, an F(ab')$_2$ fragment, a scFv fragment, or a sc(Fv)$_2$ diabody.

In some embodiments, the monoclonal antibodies and antigen-binding fragments disclosed herein bind to fibronectin with an affinity of about 2 nM to about 8 nM.

In some embodiments, the isolated monoclonal antibodies or antigen-binding fragments also bind to human fibrin fragment E. In some embodiments, the isolated monoclonal antibodies or antigen-binding fragments have an anti-angiogenic effect, but do not inhibit endothelial cell proliferation.

As used herein, the term "monoclonal antibody" refers to a population of antibody molecules that contain only one species of an antigen binding site capable of immune-reacting with a particular epitope of a polypeptide or protein. A monoclonal antibody thus typically displays a single binding affinity for the protein to which it specifically binds.

As used herein, the term "chimeric antibody" refers to an antibody that has been engineered to comprise at least one human constant region. For example, one or all (e.g., one, two, or three) of the variable regions of the light chain(s) and/or one or all (e.g., one, two, or three) of the variable regions the heavy chain(s) of a mouse antibody (e.g., a mouse monoclonal antibody) can each be joined to a human constant region, such as, without limitation an IgG1 human constant region.

"Fragment" or "antibody fragment" as the terms are used herein refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments.

"Humanized antibody," as the term is used herein, refers to an antibody that has been engineered to comprise one or more human framework regions in the variable region together with non-human (e.g., mouse, rat, or hamster) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations.

As used herein, "fully human antibodies" are antibodies or antigen binding fragments of antibodies that contain only human-derived amino acid sequences. For example, a fully human antibody may be produced from a human B-cell or a human hybridoma cell. In additional embodiments, the antibody may be produced from a transgenic animal that contains the locus for a human heavy chain immunoglobulin and a human light chain immunoglobulin, or contains a nucleic acid that encodes the heavy and light chains of a specific human antibody.

As used herein, the term "percent sequence identity" refers to the degree to which any given query sequence is the same as a subject sequence. Percentage of "sequence identity" is determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. The output is the percent identity of the subject sequence with respect to the query sequence. It is noted that a query nucleotide or amino acid sequence that aligns with a subject sequence can result in many different lengths, with each length having its own percent identity.

The term "therapeutic treatment" or "treatment" means the administration of one or more pharmaceutical agents to a subject or the performance of a medical procedure on the body of a subject (e.g., surgery, such as organ transplant or heart surgery). The term therapeutic treatment also includes an adjustment (e.g., increase or decrease) in the dose or frequency of one or more pharmaceutical agents that a subject can be taking, the administration of one or more new pharmaceutical agents to the subject, or the removal of one or more pharmaceutical agents from the subject's treatment plan.

As used herein, a "subject" is an animal, e.g., a mammal, e.g., a human, monkey, dog, cat, horse, cow, pig, goat, rabbit, or mouse.

An "effective amount" is an amount sufficient to effect beneficial or desired results. For example, a therapeutically effective amount is one that achieves the desired therapeutic effect. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 8A-8B are representations of the nucleotide and amino acid sequences of the heavy chain variable region ($V_H$) (8A) and the light chain variable region ($V_L$) (8B) of the "6E7" monoclonal antibody produced by hybridoma deposited at the American Type Culture Collection (ATCC) and designated as PTA-120972. The complementarity determining regions (CDRs) of the $V_H$ region are labeled as CDR-H1, CDR-H2, and CRD-H3, and the CDRs of the $V_L$ region are labeled as CDR-L1, CDR-L2, and CRD-L3.

FIGS. 9A-9B are representations of the nucleotide and amino acid sequences of the $V_H$ (9A) and $V_L$ (9B) regions of the "7A2" monoclonal antibody produced by hybridoma deposited at the ATCC and designated as PTA-120970. The CDRs of the $V_H$ region are labeled as CDR-H1, CDR-H2, and CRD-H3, and the CDRs of the VL region are labeled as CDR-L1, CDR-L2, and CRD-L3.

FIGS. 10A-10B are representations of the nucleotide and amino acid sequences of the $V_H$ (10A) and $V_L$ (10B) regions of the "7A8" monoclonal antibody produced by hybridoma deposited at the ATCC and designated as PTA-120971. The CDRs of the $V_H$ region are labeled as CDR-H1, CDR-H2, and CRD-H3. The CDRs of the $V_H$ region are labeled as CDR-H1, CDR-H2, and CRD-H3, and the CDRs of the VL region are labeled as CDR-L1, CDR-L2, and CRD-L3.

FIGS. 11A-11B are sensograms showing strong binding of 7A8 antibody to fibronectin protein.

DETAILED DESCRIPTION

Figure 1:
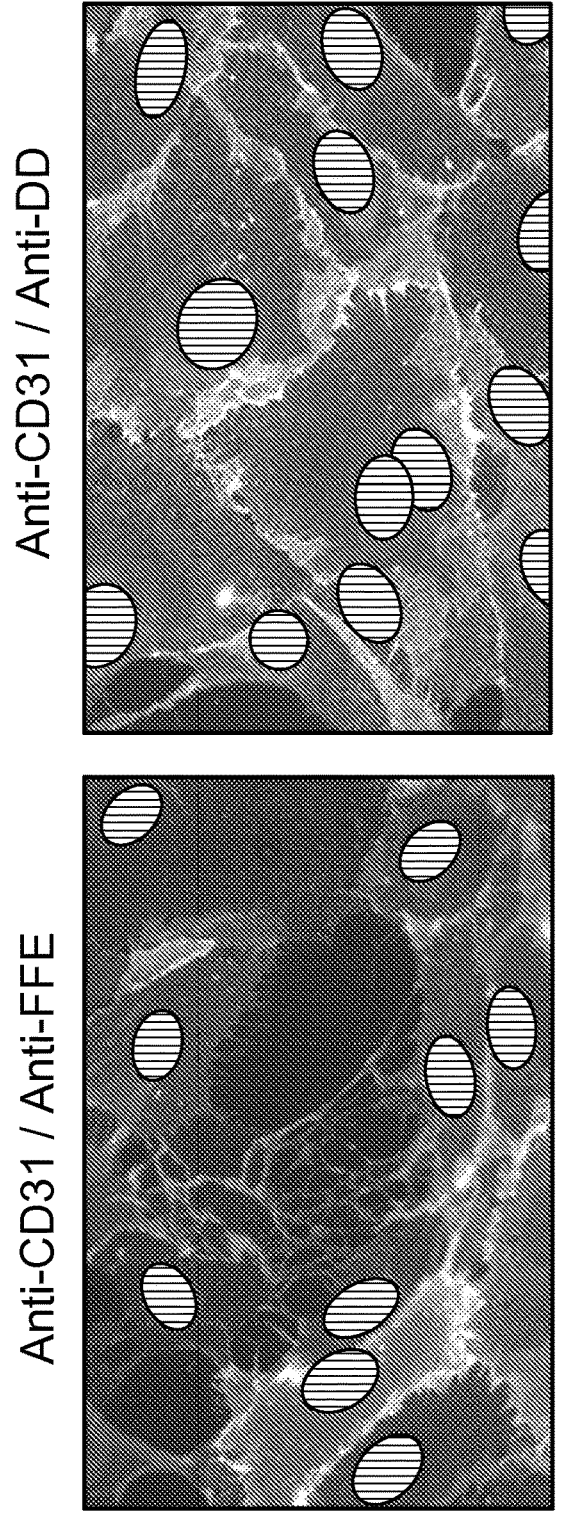
FIGS. 1A and 1B are a set of immunofluorescence images of CD 31-stained human umbilical endothelial cells (HUVEC) (crosshatched regions indicate nuclei of HUVEC) showing that a rabbit polyclonal antibody that was raised against human fibrinogen and affinity purified on immobilized human fibrin fragment E (FFE), binds to an extracellular matrix protein. This matrix protein was secreted by HUVEC (1A), since the HUVEC were grown on uncoated glass. HUVEC cell membrane was labeled with an anti-CD31 antibody. The identity of the matrix protein was established by its reactivity with antibodies to human fibronectin. By contrast, an antibody to fibrin fragment D-Dimer (anti-DD), the major component of fibrin(ogen), showed no such binding to fibronectin (1B).

The present disclosure is based, at least in part, on the development of new monoclonal antibodies that selectively and specifically bind to both fibronectin and either fibrinogen or fibrin fragment E. These antibodies and antigen-binding fragments thereof are useful for inhibiting angiogenesis and for treating angiogenesis-related diseases, e.g., solid tumors and wet macular degeneration. Unlike other anti-angiogenic antibodies, these new antibodies do not bind or inhibit growth factors, like vascular endothelial growth factor (VEGF), and do not inhibit cell proliferation. Provided herein are these antibodies and antigen-binding fragments thereof, compositions and kits containing these antibodies and antibody fragments, and various methods of using these antibodies and antigen-binding fragments.

The term monoclonal antibody refers to a population of antibody molecules that contain only one species of an antigen binding site capable of immune-reacting with a particular epitope of a polypeptide or protein. A monoclonal antibody thus typically displays a single binding affinity for the protein to which it specifically binds.

In general, a given antibody can include one of five different types of heavy chains, called alpha, delta, epsilon, gamma, and mu, the categorization of which is based on the amino acid sequence of the heavy chain constant region. These different types of heavy chains give rise to five classes of antibodies, IgA (including IgA1 and IgA2), IgD, IgE, IgG (IgG1, IgG2, IgG3, and IgG4) and IgM, respectively. A given antibody also comprises one of two types of light chains, called kappa or lambda, the categorization of which is based on the amino acid sequence of the light chain constant domains. IgG, IgD, and IgE antibodies generally contain two identical heavy chains and two identical light chains and two antigen combining domains, each composed of a heavy chain variable region ($V_H$) and a light chain variable region ($V_L$).

Antigen-binding fragments include any antibody fragments containing the active binding region of the antibody, such as a Fab fragment, a F(ab')2 fragment, or a single-chain (sc) Fv fragment. Such fragments can be produced from the antibody using techniques well established in the art (see, e.g., Rousseaux et al., in Methods Enzymol., 121:663-69 Academic Press, (1986)). For example, the F(ab')2 fragments can be produced by pepsin digestion of the antibody molecule, and the Fab fragments can be generated by reducing the disulphide bridges of the F(ab')2 fragments.

Additional types of antibody fragments include, for example, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Another example is aptamers, peptide or nucleotide structures that bind to an antigen epitope like an antibody. Additional examples of antigen-binding antibody fragments are known in the art.

"Diabody" refers to a bivalent antibody fragment constructed by gene fusion (see Holliger et. al., 1993, Proc. Natl. Acad. Sci. USA 90: 6444-6448; EP 404,097; WO 93111161). Diabodies are dimers composed of two polypeptide chains. In each of the polypeptide chains forming a dimer, a $V_L$ and a $V_H$ are generally linked by a linker in the same chain. In general, a linker in a diabody is short enough such that the $V_L$ and $V_H$ cannot bind to each other. Specifically, the number of amino acid residues constituting the linker is, for example, about five residues. Thus, the $V_L$ and $V_H$ encoded on the same polypeptide cannot form a single-chain variable region fragment, and will form a dimer with another single-chain variable region fragment. As a result, the diabody has two antigen binding sites. ScFv antibodies are single-chain polypeptides produced by linking $V_H$ and $V_L$ via a linker or such (Huston, J. S. et al., Proc. Natl. Acad. Sci. U.S.A. (1988) 85, 5879-5883; Pluckthun "The Pharmacology of Monoclonal Antibodies" Vol. 113, eds., Resenburg and Moore, Springer Verlag, New York, pp. 269-315, 1994). The H-chain V region and L-chain V region of scFv may be derived from any antibody described herein. The peptide linker for linking the V regions is not particularly limited. For example, an arbitrary single-chain peptide containing about three to 25 residues can be used as the linker.

Fibrinogen and Fibrin Degradation Products

The present disclosure provides monoclonal antibodies that specifically bind to both fibrinogen and fibronectin. Fibrinogen is a soluble, 340 kD plasma glycoprotein, that is converted by thrombin into fibrin during blood clot formation. During blood coagulation, a coagulation cascade activates the zymogen prothrombin by converting it into the serine protease thrombin. Thrombin then converts the soluble fibrinogen into insoluble fibrin strands. These fibrin strands are then cross-linked by transglutaminase Factor XIII to form a fibrin mesh, the main component of a blood clot.

The amino acid sequence of the human fibrinogen protein (Genbank Accession No. CAA50740.1) is shown below.

```
                                                      (SEQ ID NO: 35)
  1    MQNGAGASRT STIFLNGNRE RPLNVFCDME TDGGGWLVFQ RRMDGQTDFW

51    RDWEDYAHGF GNISGEFWLG NEALHSLTQA GDYSIRVDLR AGDEAVFAQY

101    DSFHVDSAAE YYRLHLEGYH GTAGDSMSYH SGSVFSARDR DPNSLLISCA

151    VSYRGAWWYR NCHYANLNGL YGSTVDHQGV SWYHWKGFEF SVPFTEMKLR

201    PRNFRSPAGG G
```

Fibrinolysis is a process during which a fibrin blood clot is broken down by the protease, plasmin. Plasmin cuts fibrin mesh at specific locations, leading to the production of circulating fibrin fragments that are cleared by other proteases or by the kidney and liver. Degradation of fibrin by plasmin yields two main soluble fragments: fibrin fragment E (FFE) and D-dimer, the heavier component. FFE has been shown to stimulate neovascularization in a chick chorioallantoic membrane assay of angiogenesis (Thompson et al., J Pathol. 168: 47-53, 1992) and contains the plasminogen binding site responsible for promoting the activation of plasminogen to plasmin by the intrinsic activity of plasminogen activator, prourokinase (Liu and Gurewich, Biochemistry, 31:6311-17, 1992). Both prourokinase and plasminogen are strongly up-regulated in angiogenesis.

Fibronectin

Fibronectin is a large glycoprotein that exists in blood, on the surface of cultured cells, or in the extracellular matrix of a tissue. Two types of fibronectin are present in vertebrates: the soluble plasma fibronectin and the insoluble cellular fibronectin. While the soluble plasma fibronectin is a major protein component of circulating blood plasma, the insoluble cellular fibronectin is a major component of the extracellular matrix. Cellular fibronectin is secreted by various cells as a soluble protein and is then assembled into an insoluble matrix in a complex cell-mediated process.

Fibronectin contains two fibrin-binding sites in its N-terminal domain, and plays important role in wound healing. During wound healing, plasma fibronectin is deposited at the site of injury along with fibrin, forming a blood clot that stops bleeding and protects the underlying tissue. The interaction between fibronectin and fibrin is mediated by Factor XIII transglutaminase and is important for cell adhesion or migration into the blood clot. As repair of the injured tissue continues, fibroblasts and macrophages begin to remodel the area by degrading the proteins that form the provisional blood clot matrix and replacing them with a matrix that more resembles the normal, surrounding tissue. During this process, plasma fibronectin was degraded as part of the provisional blood clot and then cellular fibronectin was secreted and assembled into an insoluble matrix.

Fibronectin is necessary for embryogenesis due to its role in guiding cell attachment and migration during embryonic development. Deletion of fibronectin gene during mammalian development results in early embryonic lethality, and defects in mesodermal, neural tube, and vascular development (George et al., Development 119 (4): 1079-91, 1993).

The amino acid sequence of the human fibronectin protein (Genbank Accession No. AAD00019.1) is shown below.

```
                                                      (SEQ ID NO: 36)
  1    TFDNLSPGLE YNVSVYTVKD DKESVPISDT IIPAVPPPTD LRFTNIGPDT

51    MRVTWAPPPS IDLTNFLVRY SPVKNEEDVA ELSISPSDNA VVLTNLLPGT

101    EYVVSVSSVY EQHESTPLRG RQKTGLDSPT GIDFSDITAN SFTVHWIAPR

151    ATITGYRIRH HPEHFSGRPR EDRVPHSRNS ITLTNLTPGT EYVVSIVALN

201    GREESPLLIG QQSTVSDVPR DLEVVAATPT SLLISWDAPA VTVRYYRITY

251    GETGGNSPVQ EFTVPGSKST ATISGLKPGV DYTITVYAVT GRGDSPASSK

301    PISINYRTEI DKPSQMQVTD VQDNSISVKW LPSSSPVTGY RVTTTPKNGP

351    GPTKTKTAGP DQTEMTIEGL QPTVEYVVSV YAQNPSGESQ PLVQTAVTTI

401    PAPTDLKFTQ VTPTSLSAQW TPPNVQLTGY RVRVTPKEKT GPMKEINLAP

451    DSSSVVVSGL MVATKYEVSV YALKDTLTSR PAQGVVTTLE NVSPPRRARV

501    TDATETTITI SWRTKTETIT GFQVDAVPAN GQTPIQRTIK PDVRSYTITG

551    LQPGTDYKIY LYTLNDNARS SPVVIDASTA IDAPSNLRFL ATTPNSLLVS

601    WQPPRARITG YIIKYEKPGS PPREVVPRPR PGVTEATITG LEPGTEYTIY
```

```
-continued
651   VIALKNNQKS  EPLIGRKKTV  QKTPFVTHPG  YDTGNGIQLP  GTSGQQPSVG

701   QQMIFEEHGF  RRTTPPTTAT  PIRHRPRPYP  PNVGQEALSQ  TTISWAPFQD

751   TSEYIISCHP  VGTDEEPLQF  RVPGTSTSAT  LT
```

Generation of the New Monoclonal Antibodies

The monoclonal antibodies disclosed herein can be generated by immunizing an animal (e.g., mice, rats, rabbits, goats, horses, or other mammals) with an immunogen. The immunogen to be used includes a purified and isolated fibrinogen, e.g., human fibrinogen. At the appropriate time after immunization, e.g., when the antibody titers are at a sufficiently high level, antibody producing cells, e.g., splenocytes, can be harvested, isolated and used to prepare monoclonal antibodies using standard techniques. For example, the antibody producing cells can be fused by standard somatic cell fusion procedures with immortalizing cells such as myeloma cells to yield hybridoma cells. Such techniques are well known in the art, and include, for example, the hybridoma technique as originally developed by Kohler and Milstein (Nature, 256: 495-497, 1975), the human B cell hybridoma technique (Kozbar et al., Immunology Today, 4: 72, 1983), and the EBV-hybridoma technique to produce human monoclonal antibodies (Cole et al., Monoclonal Antibodies and Cancer Therapy, Alan R. Liss, Inc. pp. 77-96, 1985).

Monoclonal antibodies can also be made by harvesting antibody producing cells, e.g., splenocytes, from transgenic mice expressing human immunoglobulin genes and which have been immunized with purified or isolated human fibrinogen or human fibronectin. The splenocytes can be immortalized through fusion with human myelomas or through transformation with Epstein-Barr virus (EBV). These hybridomas can be made using human B cell- or EBV-hybridoma techniques described in the art (see, e.g., Boyle et al., European Patent Publication No. 614,984).

Hybridoma cells producing a monoclonal antibody that binds to both fibronectin and fibrinogen are detected by screening the hybridoma culture supernatants, e.g., using the enzyme-linked immunosorbent assays (ELISA). In some embodiments, a target monoclonal antibody reacts strongly with both fibrinogen (Fg) and fibronectin (FN). In some embodiments, a target monoclonal antibody reacts strongly with FN, and one of the following: fibrin fragment E (FFE), fibrinogen or its fragment E domain.

Hybridoma cells that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (see, e.g., R. H. Kenneth, in Monoclonal Antibodies: A New Dimension In Biological Analyses, Plenum Publishing Corp., New York, N.Y., 1980). Conditioned hybridoma culture supernatant containing the antibody can then be collected.

The new monoclonal antibodies disclosed herein can be extracted from the culture supernatant containing the antibodies using methods generally applied for protein isolation and purification, for example, ammonium sulfate salting out, ion exchange chromatography, column chromatography using molecular sieve gel, affinity column chromatography using protein A binding polysaccharides, dialysis, and lyophilization.

The monoclonal antibodies disclosed herein can also be engineered by constructing a recombinant combinatorial immunoglobulin library and screening the library with human Fg and FN. Kits for generating and screening phage display libraries are commercially available (e.g., the Pharmacia Recombinant Phage Antibody System, Catalog No. 27-9400-01; and the Stratagene SurfZAP® Phage Display Kit, Catalog No. 240612). Briefly, the antibody library is screened to identify and isolate phages that express an antibody that binds to human Fg and FN. In some embodiments, the antibody library is screened to identify and isolate phages that express an antibody that binds to human Fg, FN and FFE. In certain embodiments, the primary screening of the library involves screening with immobilized human Fg, FN, and/or FFE protein.

Following screening, the display phage is isolated and the nucleic acid encoding the selected antibody can be recovered from the display phage (e.g., from the phage genome) and sub-cloned into other expression vectors by well-known recombinant DNA techniques. The nucleic acid can be further manipulated (e g, linked to nucleic acid encoding additional immunoglobulin domains, such as additional constant regions) and/or expressed in a host cell.

New Monoclonal Antibodies

Provided herein are novel monoclonal antibodies and antigen-binding fragments that (1) bind to both human fibronectin and human fibrinogen, and (2) bind competitively with at least one of the monoclonal antibodies produced by the hybridoma deposited at the American Type Culture Collection (ATCC) and designated as PTA-120972 (the 6E7 antibody), PTA-120970 (the 7A2 antibody), or PTA-120971 (the 7A8 antibody).

In some embodiments, the monoclonal antibodies and antigen-binding fragments disclosed herein recognize the same epitope as recognized by the 6E7 antibody. In some embodiments, the monoclonal antibodies and antigen-binding fragments disclosed herein recognize the same epitope as recognized by the 7A2 antibody. In some embodiments, the monoclonal antibodies and antigen-binding fragments disclosed herein recognize the same epitope as recognized by the 7A8 antibody.

In some embodiments, the monoclonal antibodies and antigen-binding fragments disclosed herein comprise the heavy and/or light chain (or a fragment thereof) of the 6E7, 7A2, or 7A8 antibodies. In some embodiments, the monoclonal antibodies and antigen-binding fragments described herein comprises the heavy and/or light chain variable region (or a fragment thereof) of the 6E7, 7A2, or 7A8 antibodies.

As known in the art, an antibody's specificity towards a given antigen is mediated by the heavy and light chain variable regions. In particular, the specificity of an antibody towards a given antigen is primarily determined by short sequences within the heavy and light chain variable regions called complementarity determining regions, or CDRs.

Provided herein are the nucleotide and amino acid sequences of the heavy and light chain variable regions and the heavy and light chain CDRs of the monoclonal antibodies produced by the hybridoma deposited at the ATCC and designated as PTA-120972 (the 6E7 antibody), PTA-120970 (the 7A2 antibody), or PTA-120971 (the 7A8 antibody).

The amino acid sequence of antibody 6E7's heavy chain variable region is shown below. CDR1 (SEQ ID NO:4), CDR2 (SEQ ID NO:6), and CDR3 (SEQ ID NO:8) of the heavy chain variable region (V$_H$) are shown in that order from N to the C-terminus of the V$_H$ sequence and are underlined and bolded.

QVQLQQPGSVLVRPGASVKLSCKASGYTFTSYWMHWAKQRPGQGL

EWIGQIHPISGNIKYNEKFKGKATLTVDTSPSTAYVDLSSLTSED

SAVYYCARDTYYTNNDAVDYWGQGTSVTVSS (V$_H$ of 6E7; SEQ ID NO: 2)

The amino acid sequence of the light chain variable region of antibody 6E7 is shown below. CDR1 (SEQ ID NO:12), CDR2 (SEQ ID NO:14), and CDR3 (SEQ ID NO:16) of the light chain variable region (V$_L$) are shown in that order from N to the C-terminus of the V$_L$ sequences and are underlined and bolded.

DIVMTQSHKFMSTSVGDRVSITCKASQDVGSVVA
WYQQKPGQSPKLLIYWASTRHTGIPNRFTGRG
SGTDFTLTITNVQSEDLADYFCQQYSNYPLTF
GAGTKLELK (V$_L$ of 6E7; SEQ ID NO:10)

The nucleotide and amino acid sequences of the V$_H$ and V$_L$ CDRs of antibody 6E7 are shown in Table 1.

TABLE 1

| 6E7CDRs | Nucleotide sequence | Protein Sequence | # residues |
|---|---|---|---|
| V$_H$ CDR-1 | ggctacaccttcacc agctactggatgcac (SEQ ID NO: 3) | GYTFTSYWMH (SEQ ID NO: 4) | 10 |
| V$_H$ CDR-2 | cagatccatcctatt agtggtaatattaag tacaatgagaagttc aagggc (SEQ ID NO: 5) | QIHPISGNIKYNEKF KG (SEQ ID NO: 6) | 17 |
| V$_H$ CDR-3 | gatacttactatact aataacgatgctgtg gactac (SEQ ID NO: 7) | DTYYTNNDAVDY (SEQ ID NO: 8) | 12 |
| V$_L$ CDR-1 | aaggccagtcaggat gtgggtagtgttgta gcc (SEQ ID NO: 11) | KASQDVGSVVA (SEQ ID NO: 12) | 11 |
| V$_L$ CDR-2 | tgggcatccacccgg catact (SEQ ID NO: 13) | WASTRHT (SEQ ID NO: 14) | 7 |
| V$_L$ CDR-3 | cagcaatatagcaac tatcctctcacg (SEQ ID NO: 15) | QQYSNYPLT (SEQ ID NO: 16) | 9 |

The amino acid sequence of antibody 7A2's heavy chain variable region is shown below. CDR1 (SEQ ID NO:20), CDR2 (SEQ ID NO:22), and CDR3 (SEQ ID NO:24) of the V$_H$ domain are shown in that order from N to the C-terminus of the V$_H$ sequence and are underlined and bolded.

QVQLRESEPGLVAPSQSLSITCTVSGFSLTSYAVSWVRQPPGKGL

EWLGVIWTGGGTNYNSALKSRLSISRDNSKNQVFLKMNSLQTDDT

ARYYCARYSNLYYAMDYWGQGTSVTVSS (V$_H$ of 7A2; SEQ ID NO: 18)

The amino acid sequence of the light chain variable region of antibody 7A2 is shown below. CDR1 (SEQ ID NO:28), CDR2 (SEQ ID NO:30), and CDR3 (SEQ ID NO:32) of the light chain variable region (V$_L$) are shown in that order from N to the C-terminus of the VL sequences and are underlined and bolded.

DIVMTQSQKFMSTSVGERVSITCKASQNVGTNVAWYQQKAGQSLE

LLIYGASNRHTGVPDRFTGSGSGTDFTLTITNVQSEDMTNYFCEQ

YRSYPLTFGGGSKLEIK (V$_L$ of 7A2; SEQ ID NO: 26)

The nucleotide and amino acid sequences of the V$_H$ and V$_L$ CDRs of antibody 7A2 are shown in Table 2.

TABLE 2

| 7A2CDRS | Nucleotide sequence | Protein Sequence | # residues |
|---|---|---|---|
| V$_H$ CDR-1 | gggttctcattaacca gctatgctgtaagc (SEQ ID NO: 19) | GFSLTSYAVS (SEQ ID NO: 20) | 10 |
| V$_H$ CDR-2 | gtaatatggactggtg gaggcacaaattataa tccagctctcaaatcc (SEQ ID NO: 21) | VIWTGGGTNYNSA LKS (SEQ ID NO: 22) | 16 |
| V$_H$ CDR-3 | tatagtaacctttact atgctatggactac (SEQ ID NO: 23) | YSNLYYAMDY (SEQ ID NO: 24) | 10 |
| V$_L$ CDR-1 | aaggccagtcagaatg taggtactaatgttgc c (SEQ ID NO: 27) | KASQNVGTNVA (SEQ ID NO: 28) | 11 |
| V$_L$ CDR-2 | ggggcatccaaccggc acact (SEQ ID NO: 29) | GASNRHT (SEQ ID NO: 30) | 7 |
| V$_L$ CDR-3 | gaacaatataggagct atcctctgacg (SEQ ID NO: 31) | EQYRSYPLT (SEQ ID NO: 32) | 9 |

The amino acid sequence of antibody 7A8's the heavy chain variable region is shown below. CDR1 (SEQ ID NO:20), CDR2 (SEQ ID NO:22), and CDR3 (SEQ ID NO:24) of the heavy chain variable region (V$_H$) are shown in that order from N to the C-terminus of the V$_H$ sequence and are underlined and boldened.

QVQLRESEPGLVAPSRSLSITCTVSGFSLTSYAVSWVRQPPGKGL

EWLGVIWTGGGTNYNSALKSRLSISKDNSKNQVFLKMNSLQTDDT

ARYYCARYSNLYYAMDYWGQGTSVTVSS (V$_H$ of 7A8; SEQ ID NO: 34)

The amino acid sequence of the light chain variable region of antibody 7A8 is shown below. CDR1 (SEQ ID NO:28), CDR2 (SEQ ID NO:30), and CDR3 (SEQ ID NO:32) of the light chain variable region (V$_L$) are shown in that order from N to the C-terminus of the VL sequences and are underlined and boldened.

DIVMTQSQKFMSTSVGERVSITCKASQNVGTNVAWYQQKAGQSLE

LLIYGASNRHTGVPDRFTGSGSGTDFTLTITNVQSEDMTNYFCEQ

YRSYPLTFGGGSKLEIK (V$_L$ of 7A8; SEQ ID NO: 26)

The nucleotide and amino acid sequences of antibody 7A8's CDRs are the identical to that of the antibody 7A2 as listed in Table 2. The amino acid sequences of the heavy and the light chain CDRs of the monoclonal antibodies 6E7, 7A2, and 7A8 are compared in Table 3.

TABLE 3

Alignment of the Heavy and Light Chain CDRs of Antibodies 6E7, 7A2, and 7A8

Heavy Chain CDRs $V_H$ CDR-1

|   |   |   |
|---|---|---|
| | * *** | |
| 6E7 | GYTFTSYWMH | (SEQ ID NO: 4) |
| 7A2 | GFSLTSYAVS | (SEQ ID NO: 20) |
| 7A8 | GFSLTSYAVS | (SEQ ID NO: 20) |

$V_H$ CDR-2

|   |   |   |
|---|---|---|
| | * ** * | |
| 6E7 | QIHPISGNIKYNEKFKG | (SEQ ID NO: 6) |
| 7A2 | VIWTGGGTNYNSALKS | (SEQ ID NO: 22) |
| 7A8 | VIWTGGGTNYNSALKS | (SEQ ID NO: 22) |

$V_H$ CDR-3

|   |   |   |
|---|---|---|
| | *  * ** | |
| 6E7 | DTYYTNNDAVDY | (SEQ ID NO: 8) |
| 7A2 | YSNLYYAMDY | (SEQ ID NO: 24) |
| 7A8 | YSNLYYAMDY | (SEQ ID NO: 24) |

Light Chain CDRs $V_L$ CDR-1

|   |   |   |
|---|---|---|
| | **** ** ** | |
| 6E7 | KASQDVGSVVA | (SEQ ID NO: 12) |
| 7A2 | KASQNVGTNVA | (SEQ ID NO: 28) |
| 7A8 | KASQNVGTNVA | (SEQ ID NO: 28) |

$V_L$ CDR-2

|   |   |   |
|---|---|---|
| | ** *** | |
| 6E7 | WASTRHT | (SEQ ID NO: 14) |
| 7A2 | GASNRHT | (SEQ ID NO: 30) |
| 7A8 | GASNRHT | (SEQ ID NO: 30) |

$V_L$ CDR-3

|   |   |   |
|---|---|---|
| | ** **** | |
| 6E7 | QQYSNYPLT | (SEQ ID NO: 16) |
| 7A2 | EQYRSYPLT | (SEQ ID NO: 32) |
| 7A8 | EQYRSYPLT | (SEQ ID NO: 32) |

* = conserved residue

Table 3 shows the monoclonal antibodies 6E7, 7A2, and 7A8 share some conserved amino acid residues in the heavy chain CDRs. For example, the $V_H$ CDR1 share the amino acid sequence of G-Y/F-T/S-Xa-T-S-Y (SEQ ID NO: 37); $V_H$ CDR2 share the sequence of G-Xa-Xa-Xa-Y-N-Xa-Xa-Xa-K (SEQ ID NO: 38); $V_H$ CDR3 share the sequence of Y-Xa-Xa-Xa-Xa-A-Xa-D-Y (SEQ ID NO: 39). Xa can be any amino acid residues.

Table 3 further shows the light chain CDRs of the monoclonal antibodies 6E7, 7A2, and 7A8 are highly conserved: $V_L$ CDR1 share the amino acid sequence of K-A-S-Q-D/N-V-G-S/T-Xa-V-A (SEQ ID NO: 40); $V_L$ CDR2 share the sequence of A-S-Xa-R-H-T (SEQ ID NO: 41); $V_L$ CDR3 share the sequence of Q-Y-Xa-Xa-Y-P-L-T (SEQ ID NO: 42). Xa can be any amino acid residues. Table 3 again shows that the 7A2 and 7A8 antibodies share identical amino acid sequences for all six CDRs.

In some embodiments, the monoclonal antibodies and antigen-binding fragments disclosed herein (1) bind to both human fibronectin and human fibrinogen, and (2) comprise the following heavy chain CDRs: (i) the heavy chain CDR1 comprises the amino acid sequence of SEQ ID NO:4 or the amino acid sequence of SEQ ID NO:4 with a substitution at one, two, or three amino acid positions, (ii) the heavy chain CDR2 comprises the amino acid sequence of SEQ ID NO:6 or the amino acid sequence of SEQ ID NO:6 with a substitution at one, two, or three amino acid positions, and (iii) the heavy chain CDR3 comprises the amino acid sequence of SEQ ID NO:8 or the amino acid sequence of SEQ ID NO:8 with a substitution at one, two, or three amino acid positions. In some embodiments, no amino acid substitutions are present in any of the above described heavy chain CDR1-3. In some embodiments, the one, two or three amino acid substitutions are made in positions other than those positions where a conserved amino acid residue is observed in the heavy chain CDR1-3 of 6E7, 7A2, and 7A8. For example, the one, two or three amino acid substitutions are not made at any of the following positions: positions 1, 5, 6, 7 of SEQ ID NO:4; positions 7, 11, 12, 16 of SEQ ID NO:6; or positions 3, 9, 11, 12 of SEQ ID NO:8.

In some embodiments, the one, two, or three amino acid substitutions are made based on the similarity in polarity, charge, solubility, hydrophobicity, hydrophilicity, and/or the amphipathic nature of the residues involved. Nonpolar (hydrophobic) amino acids include alanine, leucine, isoleucine, valine, proline, phenylalanine, tryptophan, and methionine. Polar neutral amino acids include glycine, serine, threonine, cysteine, tyrosine, asparagine, and glutamine. Positively charged (basic) amino acids include arginine, lysine, and histidine. Negatively charged (acidic) amino acids include aspartic acid and glutamic acid. Substitutions of the amino acid residues are preferably conservative substitutions, e.g., a residue is replaced by another residue with the same polarity and/or charge.

In some embodiments, the one, two, or three amino acid substitutions are conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Conservative amino acid substitutions typically include substitutions within the same family. In some embodiments, the monoclonal antibodies and antigen-binding fragments disclosed herein comprise the heavy chain CDR1-3 described above and one or more of the light chain CDRs described herein.

In some embodiments, the monoclonal antibodies and antigen-binding fragments disclosed herein (1) bind to both human fibronectin and human fibrinogen, and (2) comprise the following light chain CDRs: (i) the light chain CDR1 comprises the amino acid sequence of SEQ ID NO:12 or the amino acid sequence of SEQ ID NO:12 with a substitution at one, two, or three amino acid positions, (ii) the light chain CDR2 comprises the amino acid sequence of SEQ ID NO:14 or the amino acid sequence of SEQ ID NO:14 with a substitution at one, two, or three amino acid positions, and (iii) the light chain CDR3 comprises the amino acid sequence of SEQ ID NO:16 or the amino acid sequence of SEQ ID NO:16 with a substitution at one, two, or three amino acid positions. In some embodiments, no amino acid substitutions are present in any of the above described light chain CDR1-3. In some embodiments, the one, two or three amino acid substitutions are made in positions other than those positions where a conserved amino acid residue is observed in the light chain CDR1-3 of 6E7, 7A2, and 7A8. For example, the one, two or three amino acid substitutions are not made at any of the following positions: positions 1, 2, 3, 4, 6, 7, 10, 11 of SEQ ID NO:12; positions 2, 3, 5, 6, 7 of SEQ ID NO:14; or positions 2, 3, 6, 7, 8, 9 of SEQ ID NO:16. In some embodiments, the one, two, or three amino acid substitutions are conservative amino acid substitutions as described above.

In some embodiments, the monoclonal antibodies and antigen-binding fragments disclosed herein comprises the light chain CDR1-3 described above and one or more of the heavy chain CDRs described herein.

In some embodiments, the monoclonal antibodies and antigen-binding fragments disclosed herein (1) bind to both human fibronectin and human fibrinogen, and (2) comprise the following heavy and light chain CDRs: (i) the heavy chain CDR1 comprises the amino acid sequence of SEQ ID NO:4 or the amino acid sequence of SEQ ID NO:4 with a substitution at one, two, or three amino acid positions, (ii) the heavy chain CDR2 comprises the amino acid sequence of SEQ ID NO:6 or the amino acid sequence of SEQ ID NO:6 with a substitution at one, two, or three amino acid positions, (iii) the heavy chain CDR3 comprises the amino acid sequence of SEQ ID NO:8 or the amino acid sequence of SEQ ID NO:8 with a substitution at one, two, or three amino acid positions, (iv) the light chain CDR1 comprises the amino acid sequence of SEQ ID NO:12 or the amino acid sequence of SEQ ID NO:12 with a substitution at one, two, or three amino acid positions, (v) the light chain CDR2 comprises the amino acid sequence of SEQ ID NO:14 or the amino acid sequence of SEQ ID NO:14 with a substitution at one, two, or three amino acid positions, and (vi) the light chain CDR3 comprises the amino acid sequence of SEQ ID NO:16 or the amino acid sequence of SEQ ID NO:16 with a substitution at one, two, or three amino acid positions. In some embodiments, no amino acid substitutions are present in any of the above described heavy and light chain CDRs. In some embodiments, the one, two or three amino acid substitutions are made in positions other than those positions where a conserved amino acid residue is observed in the heavy or light chain CDRs of 6E7, 7A2, and 7A8. In some embodiments, the one, two, or three amino acid substitutions are conservative amino acid substitutions as described above.

In some embodiments, the monoclonal antibodies and antigen-binding fragments disclosed herein (1) bind to both human fibronectin and human fibrinogen, and (2) comprise the following heavy and light chain CDRs: (i) a heavy chain CDR1 comprising the amino acid sequence of SEQ ID NO:4, (ii) a heavy chain CDR2 comprising the amino acid sequence of SEQ ID NO:6, (iii) a heavy chain CDR3 comprising the amino acid sequence of SEQ ID NO:8, (iv) a light chain CDR1 comprising the amino acid sequence of SEQ ID NO: 12, (v) a light chain CDR2 comprising the amino acid sequence of SEQ ID NO:14, and (vi) a light chain CDR3 comprising the amino acid sequence of SEQ ID NO:16.

In some embodiments, the monoclonal antibodies and antigen-binding fragments disclosed herein (1) bind to both human fibronectin and human fibrinogen, and (2) comprise the following heavy chain CDRs: (i) the heavy chain CDR1 comprises the amino acid sequence of SEQ ID NO:20 or the amino acid sequence of SEQ ID NO:20 with a substitution at one, two, or three amino acid positions, (ii) the heavy chain CDR2 comprises the amino acid sequence of SEQ ID NO:22 or the amino acid sequence of SEQ ID NO:22 with a substitution at one, two, or three amino acid positions, and (iii) the heavy chain CDR3 comprises the amino acid sequence of SEQ ID NO:24 or the amino acid sequence of SEQ ID NO:24 with a substitution at one, two, or three amino acid positions. In some embodiments, no amino acid substitutions are present in any of the above described heavy chain CDR1-3. In some embodiments, the one, two or three amino acid substitutions are made in positions other than those positions where a conserved amino acid residue is observed in the heavy chain CDR1-3 of 6E7, 7A2, and 7A8. For example, the one, two or three amino acid substitutions are not made at any of the following positions: positions 1, 5, 6, 7 of SEQ ID NO:20; positions 6, 10, 11, 15 of SEQ ID NO:22; or positions 1, 7, 9, 10 of SEQ ID NO:24. In some embodiments, the one, two, or three amino acid substitutions are conservative amino acid substitutions as described above.

In some embodiments, the monoclonal antibodies and antigen-binding fragments disclosed herein comprises the heavy chain CDR1-3 described above and one or more of the light chain CDRs described herein.

In some embodiments, the monoclonal antibodies and antigen-binding fragments disclosed herein (1) bind to both human fibronectin and human fibrinogen, and (2) comprise the following light chain CDRs: (i) the light chain CDR1 comprises the amino acid sequence of SEQ ID NO:28 or the amino acid sequence of SEQ ID NO:28 with a substitution at one, two, or three amino acid positions, (ii) the light chain CDR2 comprises the amino acid sequence of SEQ ID NO:30 or the amino acid sequence of SEQ ID NO:30 with a substitution at one, two, or three amino acid positions, and (iii) the light chain CDR3 comprises the amino acid sequence of SEQ ID NO:32 or the amino acid sequence of SEQ ID NO:32 with a substitution at one, two, or three amino acid positions. In some embodiments, no amino acid substitutions are present in any of the above described light chain CDR1-3. In some embodiments, the one, two or three amino acid substitutions are made in positions other than those positions where a conserved amino acid residue is observed in the light chain CDR1-3 of 6E7, 7A2, and 7A8. For example, the one, two or three amino acid substitutions are not made at any of the following positions: positions 1, 2, 3, 4, 6, 7, 10, 11 of SEQ ID NO:28; positions 2, 3, 5, 6, 7 of SEQ ID NO:30; or positions 2, 3, 6, 7, 8, 9 of SEQ ID NO:32. In some embodiments, the one, two, or three amino acid substitutions are conservative amino acid substitutions as described above.

In some embodiments, the monoclonal antibodies and antigen-binding fragments disclosed herein comprises the light chain CDR1-3 described above and one or more of the heavy chain CDRs described herein.

In some embodiments, the monoclonal antibodies and antigen-binding fragments disclosed herein (1) bind to both human fibronectin and human fibrinogen, and (2) comprise the following heavy and light chain CDRs: (i) the heavy chain CDR1 comprises the amino acid sequence of SEQ ID NO:20 or the amino acid sequence of SEQ ID NO:20 with a substitution at one, two, or three amino acid positions, (ii) the heavy chain CDR2 comprises the amino acid sequence of SEQ ID NO:22 or the amino acid sequence of SEQ ID NO:22 with a substitution at one, two, or three amino acid positions, (iii) the heavy chain CDR3 comprises the amino acid sequence of SEQ ID NO:24 or the amino acid sequence of SEQ ID NO:24 with a substitution at one, two, or three amino acid positions, (iv) the light chain CDR1 comprises the amino acid sequence of SEQ ID NO:28 or the amino acid sequence of SEQ ID NO:28 with a substitution at one, two, or three amino acid positions, (v) the light chain CDR2 comprises the amino acid sequence of SEQ ID NO:30 or the amino acid sequence of SEQ ID NO:30 with a substitution at one, two, or three amino acid positions, and (vi) the light chain CDR3 comprises the amino acid sequence of SEQ ID NO:32 or the amino acid sequence of SEQ ID NO:32 with a substitution at one, two, or three amino acid positions. In some embodiments, no amino acid substitutions are present in any of the above described heavy and light chain CDRs. In some embodiments, the one, two or three amino acid substitutions are made in positions other than those positions where a conserved amino acid residue is observed in the heavy or light chain CDRs of 6E7, 7A2, and 7A8. In some embodiments, the one, two, or three amino acid substitutions are conservative amino acid substitutions as described above.

In some embodiments, the monoclonal antibodies and antigen-binding fragments disclosed herein (1) bind to both human fibronectin and human fibrinogen, and (2) comprise the following heavy and light chain CDRs: (i) a heavy chain CDR1 comprising the amino acid sequence of SEQ ID NO:20, (ii) a heavy chain CDR2 comprising the amino acid sequence of SEQ ID NO:22, (iii) a heavy chain CDR3 comprising the amino acid sequence of SEQ ID NO:24, (iv) a light chain CDR1 comprising the amino acid sequence of SEQ ID NO: 28, (v) a light chain CDR2 comprising the amino acid sequence of SEQ ID NO:30, and (vi) a light chain CDR3 comprising the amino acid sequence of SEQ ID NO:32.

In some embodiments, the monoclonal antibodies and antigen-binding fragments disclosed herein (1) binds to both human fibronectin and human fibrinogen, and (2) comprises the same heavy and light chain CDRs as one of the monoclonal antibodies produced by the hybridoma deposited at the ATCC and designated as PTA-120972, PTA-120970, or PTA-120971.

In some embodiments, the monoclonal antibodies and antigen-binding fragments disclosed herein (1) bind to both human fibronectin and human fibrinogen, and (2) comprise a heavy chain variable region that is at least 65%, e.g., 65%, 70%, 75%, 80%, 85%, 90%, 95%, 100%, identical to SEQ ID NO:2, and a light chain variable region that is at least 65%, e.g., 65%, 70%, 75%, 80%, 85%, 90%, 95%, 100%, identical to SEQ ID NO:10.

In some embodiments, the monoclonal antibodies and antigen-binding fragments disclosed herein (1) bind to both human fibronectin and human fibrinogen, and (2) comprise a heavy chain variable region that is at least 65%, e.g., 65%, 70%, 75%, 80%, 85%, 90%, 95%, 100%, identical to SEQ ID NO:18, and a light chain variable region that is at least 65%, e.g., 65%, 70%, 75%, 80%, 85%, 90%, 95%, 100%, identical to SEQ ID NO:26.

In some embodiments, the monoclonal antibodies and antigen-binding fragments disclosed herein bind to fibronectin with an affinity of about 2 nM to about 8 nM.

In some embodiments, the monoclonal antibodies and antigen-binding fragments disclosed herein also bind to human fibrin fragment E. In some embodiments, the monoclonal antibodies and antigen-binding fragments disclosed herein have an anti-angiogenic effect, but do not inhibit endothelial cell proliferation. Combinations of two or more of the antibodies or fragments described herein are useful in any of the methods described herein.

Chimeric, Humanized, or Human Antibodies

Recombinant forms of antibodies, such as chimeric and humanized antibodies, can also be prepared to minimize the response by a human patient to the antibody. When antibodies produced in non-human subjects or derived from the expression of non-human antibody genes are used therapeutically in humans, they are recognized to varying degrees as foreign, and an immune response may be generated in the patient. One approach to minimize or eliminate this immune reaction is to produce chimeric antibody derivatives, i.e., antibody molecules that combine a non-human animal variable region and a human constant region. Such antibodies retain the epitope binding specificity of the original monoclonal antibody, but may be less immunogenic when administered to humans, and therefore more likely to be tolerated by the patient. For example, one or all (e.g., one, two, or three) of the variable regions of the light chain(s) and/or one or all (e.g., one, two, or three) of the variable regions the heavy chain(s) of a mouse antibody (e.g., a mouse monoclonal antibody) can each be joined to a human constant region, such as, without limitation an IgG1 human constant region.

Chimeric monoclonal antibodies can be produced by recombinant DNA techniques known in the art. For example, a gene encoding the constant region of a non-human antibody molecule can be substituted with a gene encoding a human constant region (see Robinson et al., PCT Patent Publication PCT/US86/02269; Akira, et al., European Patent Application 184,187; or Taniguchi, M., European Patent Application 171,496). In addition, other suitable techniques that can be used to generate chimeric antibodies are described, for example, in U.S. Pat. Nos. 4,816,567; 4,978,775; 4,975,369; and 4,816,397.

In some embodiments, chimeric versions of the monoclonal antibodies described herein can be made by replacing the constant regions of the antibodies described herein, e.g., monoclonal antibodies produced by the hybridoma PTA-120972 (the 6E7 antibody), PTA-120970 (the 7A2 antibody), or PTA-120971 (the 7A8 antibody), with a human constant region using known techniques.

A chimeric antibody can be further "humanized" by replacing portions of the variable region not involved in antigen binding with equivalent portions from human variable regions. General reviews of "humanized" chimeric antibodies are provided by Morrison, S. L. (Science 229: 1202-1207, 1985) and by Oi et al. (BioTechniques 4:214, 1986). Such methods include isolating, manipulating, and expressing the nucleic acid sequences that encode all or part of an immunoglobulin variable region from at least one of a heavy or light chain. The cDNA encoding the humanized chimeric antibody, or fragment thereof, can then be cloned into an appropriate expression vector. Suitable "humanized" antibodies can be alternatively produced by complementarity determining region (CDR) substitution (see U.S. Pat. No. 5,225,539; Jones et al., Nature 321:552-525, 1986; Verhoeyan et al., Science 239:1534, 1988; and Beidler et al., J. Immunol. 141:4053-4060, 1988).

In general, humanized antibodies are engineered to comprise one or more human framework regions in the variable region together with non-human (e.g., mouse, rat, or hamster) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations. Humanized antibodies are known in the art, and suitable techniques for generating humanized antibodies are also known. See for example, Hwang et al., Methods 36:35, 2005; Queen et al., Proc. Natl. Acad. Sci. U.S.A. 86:10029-10033, 1989; Jones et al., Nature 321:522-25, 1986; Riechmann et al., Nature 332:323-27, 1988; Verhoeyen et al., Science 239:1534-36, 1988; Orlandi et al., Proc. Natl. Acad. Sci. U.S.A. 86:3833-3837, 1989; U.S. Pat. Nos. 5,225,539; 5,530,101; 5,585,089; 5,693,761; 5,693,762; and 6,180,370; and WO 90/07861.

"Framework region" (FR) refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

In some embodiments, humanized versions of the monoclonal antibodies described herein can be made by replacing one or more (e.g., one, two, three, four, five, or six) framework regions of the antibodies described herein, e.g., monoclonal antibodies produced by the hybridoma PTA-120972 (the 6E7 antibody), PTA-120970 (the 7A2 antibody), or PTA-120971 (the 7A8 antibody), with one or more (e.g., one, two, three, four, five, or six) human framework regions.

For example, a humanized 6E7 antibody can be made by replacing one or more of the following heavy chain framework regions ($V_H$-FR) and light chain framework regions ($V_L$-FR): $V_H$-FR1 (amino acid residues 1-25 of SEQ ID NO:2), $V_H$-FR2 (amino acid residues 36-49 of SEQ ID NO:2), $V_H$-FR3 (amino acid residues 67-98 of SEQ ID NO:2), $V_H$-FR4 (amino acid residues 111-121 of SEQ ID NO:2), $V_L$-FR1 (amino acid residues 1-23 of SEQ ID NO:10), $V_L$-FR2 (amino acid residues 35-49 of SEQ ID NO:10), $V_L$-FR3 (amino acid residues 57-88 of SEQ ID NO:10), $V_L$-FR4 (amino acid residues 98-107 of SEQ ID NO:10).

A humanized 7A2 antibody can be made by replacing one or more of the following heavy and light chain framework regions: $V_H$-FR1 (amino acid residues 1-25 of SEQ ID NO:18), $V_H$-FR2 (amino acid residues 36-49 of SEQ ID NO:18), $V_H$-FR3 (amino acid residues 66-97 of SEQ ID NO:18), $V_H$-FR4 (amino acid residues 108-118 of SEQ ID NO:18), $V_L$-FR1 (amino acid residues 1-23 of SEQ ID NO:26), $V_L$-FR2 (amino acid residues 35-49 of SEQ ID NO:26), $V_L$-FR3 (amino acid residues 57-88 of SEQ ID NO:26), $V_L$-FR4 (amino acid residues 98-107 of SEQ ID NO:26).

A humanized 7A8 antibody can be made by replacing one or more of the following heavy and light chain framework regions: $V_H$-FR1 (amino acid residues 1-25 of SEQ ID NO:34), $V_H$-FR2 (amino acid residues 36-49 of SEQ ID NO:34), $V_H$-FR3 (amino acid residues 66-97 of SEQ ID NO:34), $V_H$-FR4 (amino acid residues 108-118 of SEQ ID NO:34), $V_L$-FR1 (amino acid residues 1-23 of SEQ ID NO:26), $V_L$-FR2 (amino acid residues 35-49 of SEQ ID NO:26), $V_L$-FR3 (amino acid residues 57-88 of SEQ ID NO:26), $V_L$-FR4 (amino acid residues 98-107 of SEQ ID NO:26).

Epitope imprinting can also be used to produce a "human" antibody polypeptide dimer that retains the binding specificity of the antibodies disclosed herein. Briefly, a gene encoding a non-human variable region ($V_H$) with specific binding to an antigen and a human constant region (CH1), is expressed in *E. coli* and infected with a phage library of human VλCλ genes. Phages displaying antibody fragments are then screened for binding to human FN and Fg or FFE. Selected human Vλ, genes are re-cloned for expression of VλCλ chains and *E. coli* bacteria harboring these chains are infected with a phage library of human VHCH1 genes and the library is subject to rounds of screening with antigen coated tubes (See Hoogenboom et al., PCT publication WO 93/06213).

In some embodiments, fully human antibodies of the monoclonal antibodies described herein, e.g., the monoclonal antibodies produced by the hybridoma PTA-120972 (the 6E7 antibody), PTA-120970 (the 7A2 antibody), or PTA-120971 (the 7A8 antibody), can be made using epitope imprinting.

Hybridomas

Also provided herein are novel hybridomas that produce antibodies that selectively and specifically bind to both fibronectin and either fibrinogen or fibrin fragment E. As is known the art, the term "hybridoma" refers to a cell that is produced by the fusion of an antibody-producing lymphocyte and a non-antibody-producing cancer cell, usually a myeloma or lymphoma. After fusion, hybridomas proliferate and produce the specific monoclonal antibody that was originally produced by the fused lymphocyte. In some embodiments, the hybridoma provided herein is a hybridoma deposited at the ATCC and designated as PTA-120972, PTA-120970, or PTA-120971. In some embodiments, individual cells, harvested cells, and cultures containing cells that are derived from the hybridoma PTA-120972, PTA-120970, or PTA-120971 are also provided.

Methods of Using the New Monoclonal Antibodies and Fragments

The monoclonal antibodies described herein and antigen-binding fragments thereof can be used to inhibit or reduce angiogenesis and treat angiogenesis-related disorders, e.g., a solid tumor or wet macular degeneration. Methods of treating an angiogenesis-related disorder in a subject can include (a) identifying a subject having an angiogenesis-related disorder; and (b) administering to the subject an effective amount of one or more different ones of the monoclonal antibodies disclosed herein. In some embodiments, the subject is a human. Methods of treating an angiogenesis-related disorder in a subject can further include administering to the subject a chemotherapeutic agent or a second angiogenesis inhibitor, e.g., any one or more of, but not limited to, bevacizumab, sorafenib, sunitinib, pazopanib, axitinib, cabozantinib, regorafenib, vandetanib, temsirolimus, everolimus, lenalidomide, erlotinib, angiostatin, endostatin, tumstatin, canstatin, restin, and arresten.

The angiogenesis-related disorder can be a solid tumor, for example, a sarcoma, a carcinoma, or a lymphoma. Solid tumors tend not to grow beyond a certain size, generally 1-2 mm, without formation of new blood vessels supplying oxygen and other essential nutrients and carrying away metabolic wastes. Tumors induce blood vessel growth by secreting various growth factors, e.g., vascular endothelial growth factor (VEGF) and basic fibroblast growth factor (bFGF), which in turn induce capillary growth into the tumor. Angiogenesis is also required for the metastasis of cancer cells: the process for a cancer cell to break away from an established solid tumor, enter the blood vessel, be carried to a distant site by the circulating blood, implant at the distant site, and begin to grow as a secondary tumor. Endothelial cells are genetically more stable than cancer cells. Thus, anti-angiogenic therapies targeting the endothelial cells can be advantageous when compared to chemotherapies directed at cancer cells, which can rapidly mutate and acquire drug resistance.

Angiogenesis-based tumor therapies are mainly based on targeting vascular endothelial growth factor (VEGF), the VEGF receptor, and its signaling pathways. A monoclonal antibody directed against VEGF, bevacizumab (Avastin®), was approved by Food and Drug Administration (FDA) to treat colorectal cancer in combination with other chemotherapy. Several tyrosine kinase inhibitors with anti-angiogenic activity have also been approve by FDA as anti-cancer therapies, for example, sorafenib (Nexavar®), sunitinib (Sutent®), pazopanib (Votrient®), axitinib (Inlyta®), cabozantinib (Cometriq®), regorafenib (Stivarga®), and vandetanib (Caprelsa®) (Heath et al., Nat Rev Clin Oncol. 6(7): 395-404, 2009). The FDA has also approved several other angiogenesis inhibitors as anti-cancer therapy, e.g., the mTOR inhibitors temsirolimus (Torisel®) and everolimus (Afinitor®), the thalidomide analogue lenalidomide (Revlimid®), and the EGFR inhibitor erlotinib (Tarceva®) (Cook et al., CA Cancer J Clin. 60(4):222-43, 2010). Other natural or synthetic angiogenesis inhibitors include angiostatin, endostatin, tumstatin, canstatin, restin, and arresten (Kamphaus et al., J Biol Chem. 275(2):1209-15, 2000; Sudhakar et al., Proc. Natl. Acad. Sci. U.S.A. 100 (8): 4766-71, 2003).

However, various side effects have been seen in anti-VEGF therapies, including hypertension, gastro-intestinal toxicity, hypothyroidism, proteinuria, coagulation disorders, and neurotoxicity (Roodhart et al., Curr. Clin. Pharmacol. 3(2):132-43, 2008).

On the other hand, the new monoclonal antibodies disclosed herein are not directed against a growth factor like VEGF or FGF, or against theirs receptors, and thus the toxic effects associated with known anti-VEGF therapies are not expected to arise when using the new monoclonal antibody therapies. In treating a solid tumor, the new monoclonal antibodies disclosed herein can be used alone, or in combination with one or more chemotherapeutic agent or another angiogenesis inhibitor, e.g., bevacizumab, sorafenib, sunitinib, pazopanib, axitinib, cabozantinib, regorafenib, vandetanib, temsirolimus, everolimus, lenalidomide, erlotinib, angiostatin, endostatin, tumstatin, canstatin, restin, and/or arresten. In some embodiments, the new monoclonal antibodies disclosed herein are used in combination with bevacizumab, endostatin, angiostatin, erlotinib, or herceptin, to treat solid tumor.

The angiogenesis-related disorder can also be a non-tumor disease, such as wet macular degeneration, retinopathy of diabetes mellitus. The macula is the central area of the retina, which provides the most detailed central vision. Macular degeneration results in a loss of vision in the center of the visual field, and is a major cause of blindness and visual impairment in the elderly.

Macular degeneration has a dry form and a wet form. In the dry (nonexudative) form, cellular debris called drusen accumulates between the retina and the choroid, and the retina can become detached. In the wet (exudative) form, which is more severe, abnormal blood vessels grow in the choriocapillaris behind the retina, causing blood and protein leakage below the macula. Bleeding, leaking, and scarring from these blood vessels can eventually cause irreversible damage to the photoreceptors and rapid vision loss if left untreated. The antibodies disclosed herein can be used to inhibit the abnormal blood vessel growth in treating wet macular degeneration. In these methods, the new monoclonal antibodies disclosed herein can be used alone, or in combination with one or more other angiogenesis inhibitors, for example, but not limited to, bevacizumab, sorafenib, sunitinib, pazopanib, axitinib, cabozantinib, regorafenib, vandetanib, temsirolimus, everolimus, lenalidomide, erlotinib, angiostatin, endostatin, tumstatin, canstatin, restin, and/or arresten. In some embodiments, the new monoclonal antibodies disclosed herein are used in combination with ranibizumab or pegaptanib, to treat wet macular degeneration.

Pharmaceutical Compositions, Dosage Regimen, and Methods of Administration

Any of the new monoclonal antibodies or antigen-binding fragments thereof, as well as modified antibodies or antigen-binding fragments based on such antibodies or fragments (e.g., human, chimeric or humanized antibodies or fragments), can be used as active ingredient of a pharmaceutical composition.

In some embodiments, a pharmaceutical composition provided herein can include an effective amount of at least one (e.g., one, two, three, four, five, or more different ones) of the new monoclonal antibodies or antigen-binding fragments thereof as described herein. In some embodiments, a pharmaceutical composition described herein contains one or more humanized or human version of the monoclonal antibodies produced by the hybridomas PTA-120972 (the 6E7 antibody), PTA-120970 (the 7A2 antibody), or PTA-120971 (the 7A8 antibody), or antigen-binding fragments thereof.

In some embodiments, such pharmaceutical composition can further include an effective amount of an additional angiogenesis inhibitor, e.g., bevacizumab, sorafenib, sunitinib, pazopanib, axitinib, cabozantinib, regorafenib, vandetanib, temsirolimus, everolimus, lenalidomide, erlotinib, angiostatin, endostatin, tumstatin, canstatin, restin, and arresten. In some embodiments, a pharmaceutical composition provided herein can include an effective amount of at least one (e.g., one, two, three, four, five, or more) of the isolated new antibodies or antigen-binding fragments thereof described herein, and a chemotherapeutic agent known in the art to be effective in treating cancer.

The active ingredient of a pharmaceutical composition, e.g., the new monoclonal antibodies or antigen-binding fragments thereof disclosed herein, can be formulated for delivery by any available route including, but not limited to parenteral (e.g., intravenous), intradermal, subcutaneous, oral, nasal, bronchial, ophthalmic, transdermal (topical), transmucosal, rectal, and vaginal routes. A pharmaceutical composition provided herein can include a delivery agent (e.g., a cationic polymer, peptide molecular transporter, surfactant, etc.) for the new monoclonal antibodies or fragments thereof, and a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into pharmaceutical formulations that contain an antibody or antigen-binding fragment thereof as described herein.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection can include sterile aqueous solutions (where water soluble), dispersions, and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Certain tumors may be accessible by administration by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the therapeutic compounds can be prepared with carriers that will protect the therapeutic compounds against rapid elimination from the body, such as a controlled release formulation, including implants and microencapsulated delivery systems.

In some embodiments, the pharmaceutical composition can be directly administered to the areas of active angiogenesis. In some embodiments, the pharmaceutical composition can be administered through conventional routes, e.g., intravenously. Targeting agents can be used to direct the pharmaceutical compositions to the areas of active angiogenesis. Microencapsulation technology or liposomes can be used to protect the pharmaceutical compositions during circulation and release them at the site of active angiogenesis.

The pharmaceutical compositions can be included in a container, pack, or dispenser together with instructions for administration.

The new monoclonal antibodies disclosed herein or antigen-binding fragments thereof can be administered in an effective amount, at dosages and for periods of time necessary to achieve the desired result. An "effective amount" is an amount sufficient to effect beneficial or desired results. For example, a therapeutically effective amount is one that achieves the desired therapeutic effect. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

Dosage regimens can be adjusted to provide the optimum therapeutic response. For example, several divided doses can be administered daily or the dose can be proportionally reduced as indicated by the exigencies of the therapeutic situation. Those skilled in the art will be aware of dosages and dosing regimens suitable for administration of the new monoclonal antibodies disclosed herein or antigen-binding fragments thereof to a subject. See e.g., Physicians' Desk Reference, 63rd edition, Thomson Reuters, Nov. 30, 2008. For example, Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, the monoclonal antibodies described herein are administered intravenously at about 0.1-20 mg/kg, e.g., about 0.5-15 mg/kg, about 1-12 mg/kg, about 2-10 mg/kg.

Kits

Also provided herein are kits that include at least one (e.g., two, three, four, five, or more) compositions containing at least one (e.g., one, two, three, four, five, or more different ones) of the isolated new monoclonal antibodies or antigen-binding fragments thereof described herein. In some embodiments, the kits described herein contain one or more humanized or human version of the monoclonal antibodies produced by the hybridomas PTA-120972 (the 6E7 antibody), PTA-120970 (the 7A2 antibody), or PTA-120971 (the 7A8 antibody), or antigen-binding fragments thereof.

Kits generally include the following major elements: packaging, reagents comprising binding compositions as described above, optionally a control, and instructions. Packaging can be a box-like structure for holding a vial (or number of vials) containing said binding compositions, a vial (or number of vials) containing a control, and instructions for use in a method described herein. Individuals skilled in the art can readily modify the packaging to suit individual needs.

In some embodiments, a kit provided herein can include at least one (e.g., one, two, three, four, five, or more) composition containing at least one (e.g., one, two, three, four, five, or more) of the isolated new monoclonal antibodies or antigen-binding fragments thereof described herein, e.g., one or more humanized or human version of the antibodies produced by the hybridomas PTA-120972 (the 6E7 antibody), PTA-120970 (the 7A2 antibody), or PTA-120971 (the 7A8 antibody), or antigen-binding fragments thereof, and at least one (e.g., one, two, three, four, five, or more) other composition in a separate vial containing another angiogenesis inhibitor. The angiogenesis inhibitor can be, for example, bevacizumab, sorafenib, sunitinib, pazopanib, axitinib, cabozantinib, regorafenib, vandetanib, temsirolimus, everolimus, lenalidomide, erlotinib, angiostatin, endostatin, tumstatin, canstatin, restin, and arresten. In some embodiments, a kit provided herein can include at least one (e.g., one, two, three, four, five, or more) composition containing at least one (e.g., one, two, three, four, five, or more) of the isolated new monoclonal antibodies or antigen-binding fragments thereof described herein, and at least one (e.g., one, two, three, four, five, or more) other composition in a separate vial containing a chemotherapeutic agent known in the art to be effective in treating cancer.

Compositions and kits as provided herein can be used in accordance with any of the methods (e.g., treatment methods) described above. For example, compositions and kits containing at least one (e.g., one, two, three, four, five, or more) of the isolated new monoclonal antibodies or antigen-binding fragments thereof described herein can be used to treat angiogenesis-related disorder, e.g., solid tumor or wet macular degeneration. Those skilled in the art will be aware of other suitable uses for compositions and kits provided herein, and will be able to employ the compositions and kits for such uses.

EXAMPLES

The invention is further described in the following examples, which do not limit the scope of the invention described in the claims.

Example 1. Monoclonal Antibodies Generated Against Human Fibrinogen and that Bind to FFE and Cross-React with Human Fibronectin Preparation of Fibrin Fragment E (FFE)

Fibrin fragment E (FFE) was prepared from highly purified human fibrinogen (Hyphen BioMed, Neuville-sur-Oise, France). First, human fibrinogen was lysed in the presence of plasminogen (1 mg/gram) and urokinase (uPA) (15 µg/gram). Fibrinogen degradation to fibrinogen fragments D (ffD) and E (ffE) was monitored by SDS-PAGE every 30 minutes. When all fibrinogen was degraded and ffE was at the stage of ffE1 and/or ffE2, degradation was stopped by the addition of an excess of aprotinin (Pentapharm, Basel, Switzerland). The fibrinogen fragment E (ffE) was then purified by ion exchange chromatography on DEAE Sepharose and eluted with a salt gradient in pH 6.50 Tris buffer, from 0.05 M to 0.70 M NaCl. Under these conditions, the ffD is rapidly eluted at low salt concentration, whereas ffE is retained and eluted from the column by the middle of the salt gradient, at about 0.35 M of NaCl. The ffE fractions were collected and further purified by gel permeation chromatography with a Sephacryl S100 column. The ffE fractions with a MW of 45,000 to 55,000 Daltons were collected and concentrated. SDS-PAGE showed that the preparation was a mixture of ffE1 and ffE2. Lower MW bands of ffE3 or ffE3t were absent.

The fibrinogen fragment E (ffE) was converted to fibrin fragment E (FFE) by treatment with Sepharose-immobilized human thrombin (highly purified human alpha thrombin coupled to CNBr-Activated Sepharose 4B, Amersham-Pharmacia/GE Healthcare, Uppsala, Sweden), according to the manufacturer's instructions. The ffE was recycled through the column until no more reactive ffE was in evidence (using a specific rabbit antibody targeted to the FPA moiety on ffE). After treatment with the immobilized thrombin for 30 minutes, all ffE was converted to FFE. The FFE was concentrated, dialyzed against physiological saline, and stored frozen until use.

Figure 6A:
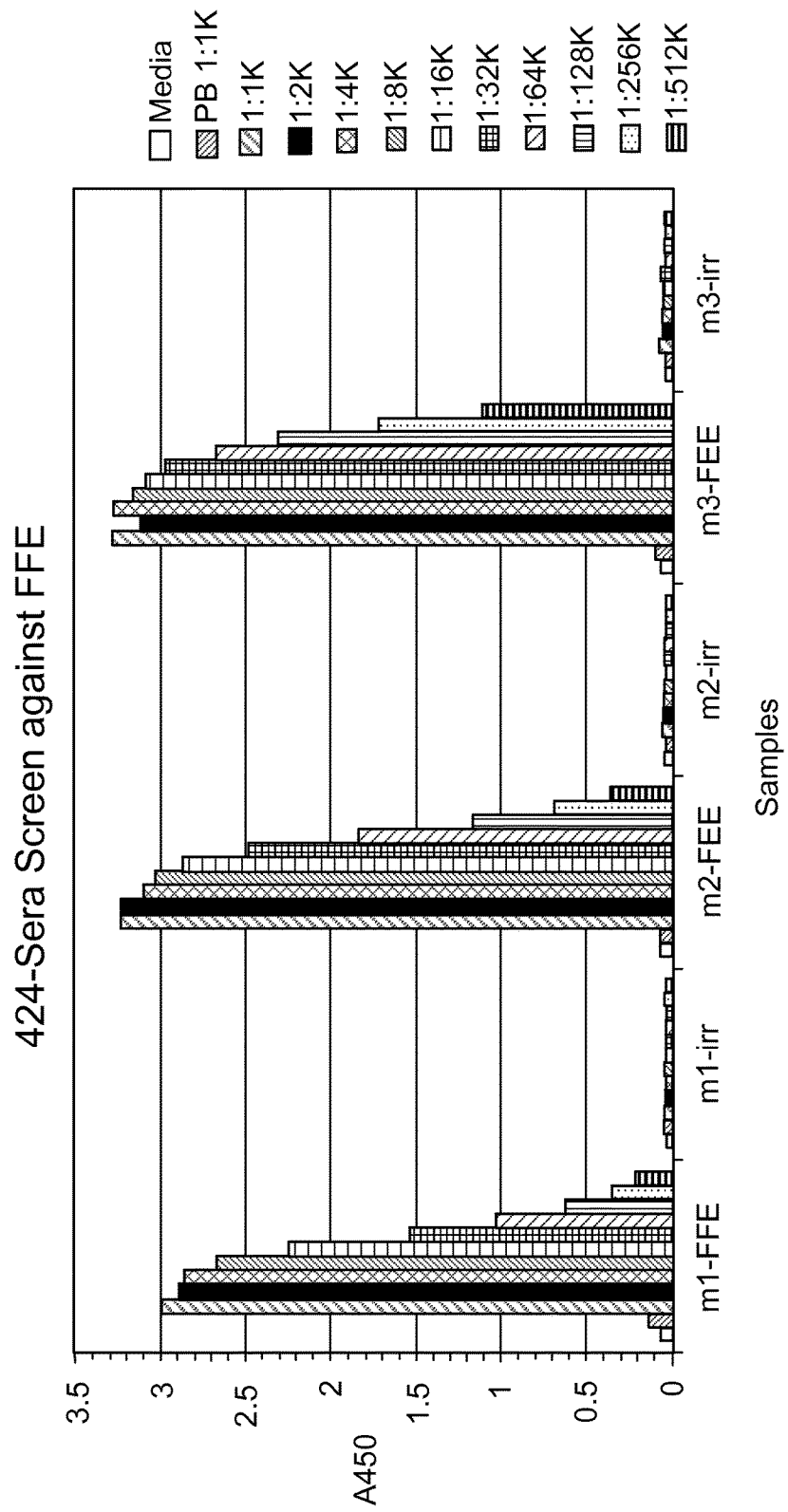
FIG. 6A is a bar graph showing enzyme-linked immunosorbent assay (ELISA) results for FFE binding by serum from three mice (m1, m2, and m3) that were immunized with highly purified human fibrinogen. The "in" is an irrelevant protein serving as a negative control for the ELISA assays.
Figure 6B:
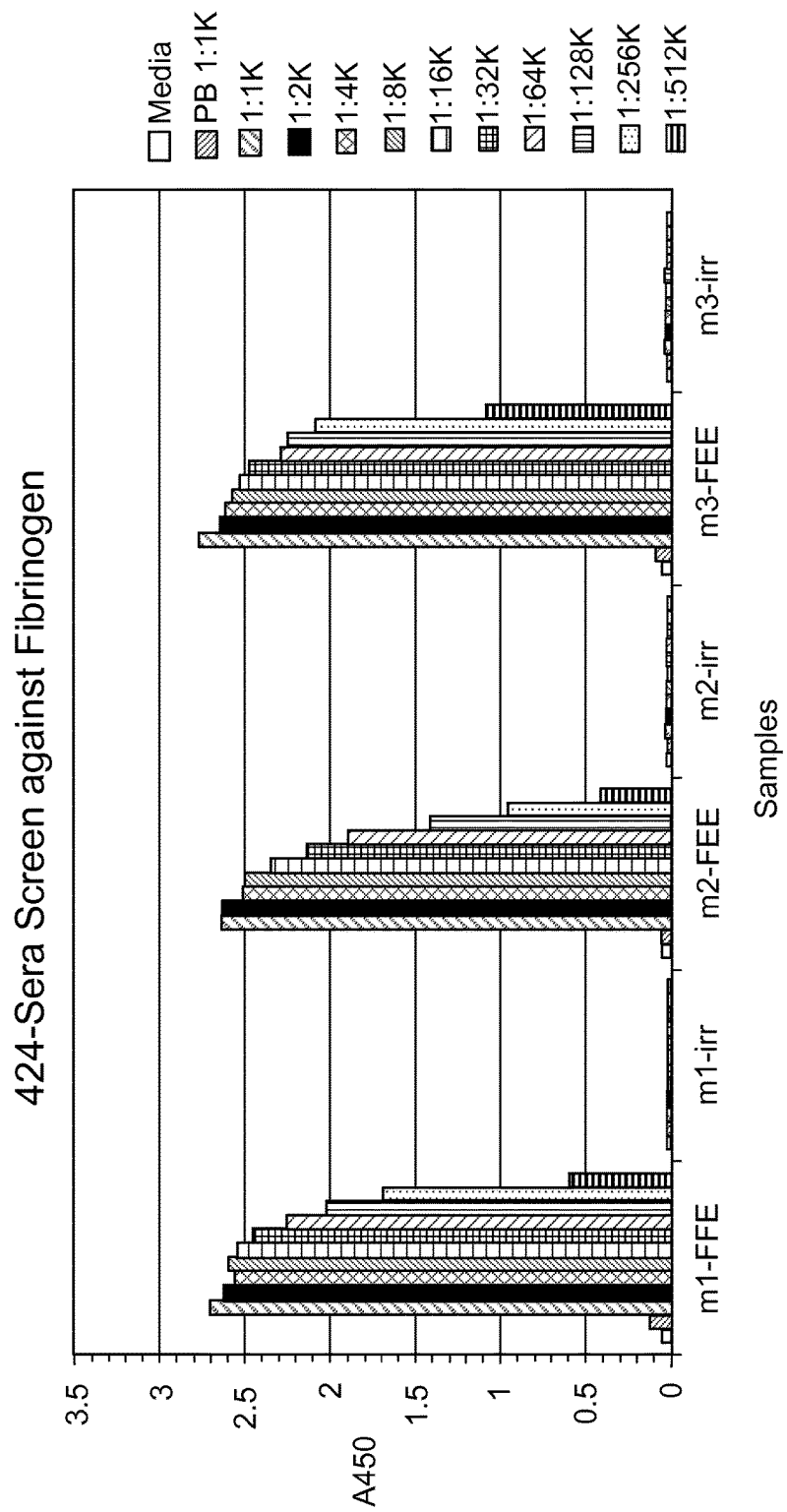
FIG. 6B is a bar graph showing ELISA results for fibrinogen binding by serum from the same mice as in FIG. 6A.
Figure 6C:
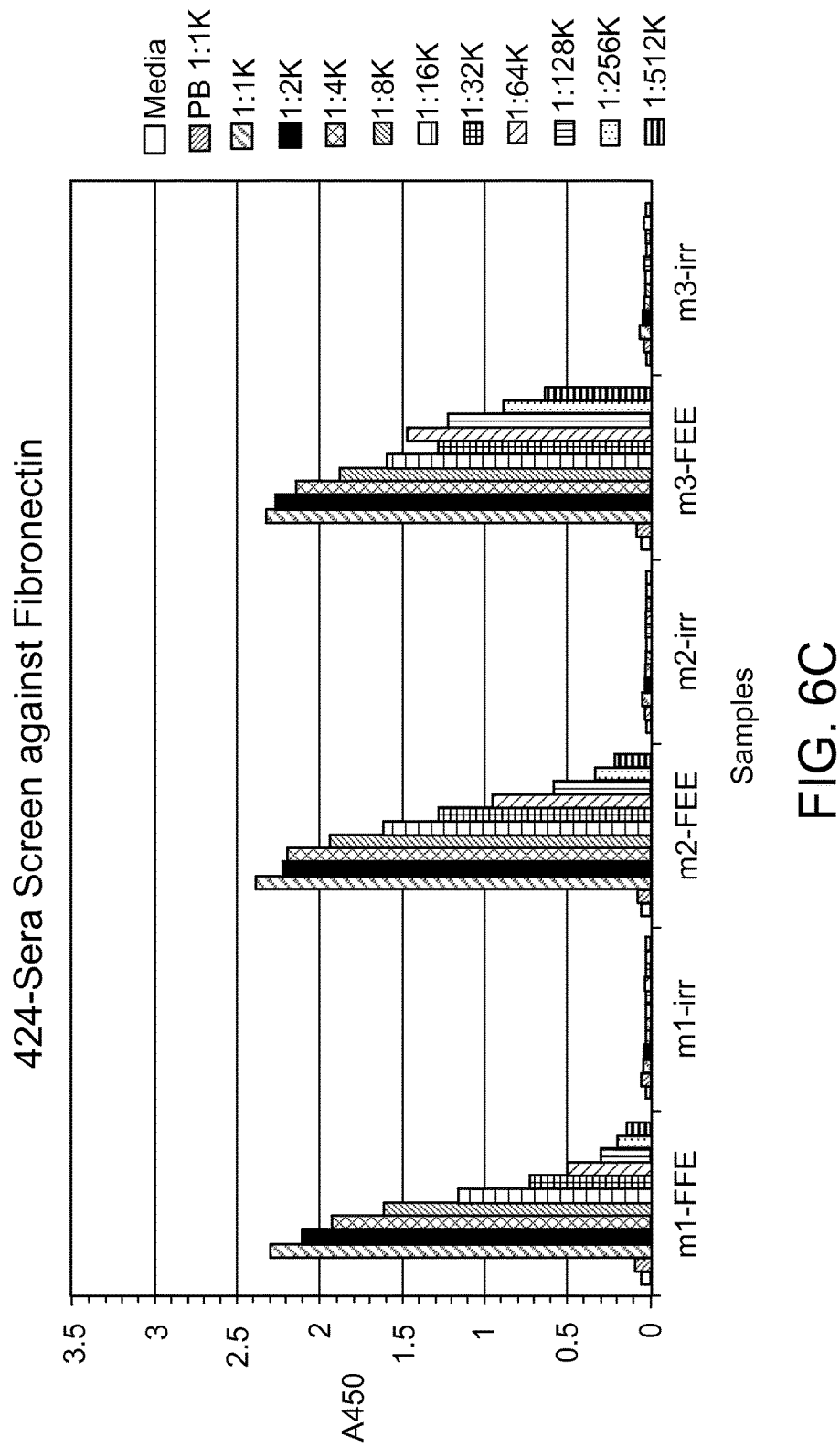
FIG. 6C is a bar graph showing ELISA results for fibronectin binding by serum from the same mice as in FIG. 6A.

Generation of Monoclonal Antibodies Raised Against Human Fibrinogen that Specifically Bind to Human Fibronectin and Human FFE Monoclonal antibodies were generated using standard protocols at the Monoclonal Antibody Core Facility of Dana Farber Cancer Institute (Boston, Mass.). Three mice were immunized by highly purified human fibrinogen (Hyphen BioMed, Neuville-sur-Oise, France). The presence of antibodies against human fibrin fragment-E (FFE) and human fibronectin in the mouse serum was detected by ELISA. FIGS. 6A-6C show the ELISA results for antibodies against human FFE, fibrinogen, and fibronectin respectively. Serum from mouse #3 (m3) showed strongest binding to human fibronectin and FFE. Splenocytes were isolated from mice #3 and fused with mouse myeloma cell line by PEG (Sigma).

Figure 6D:
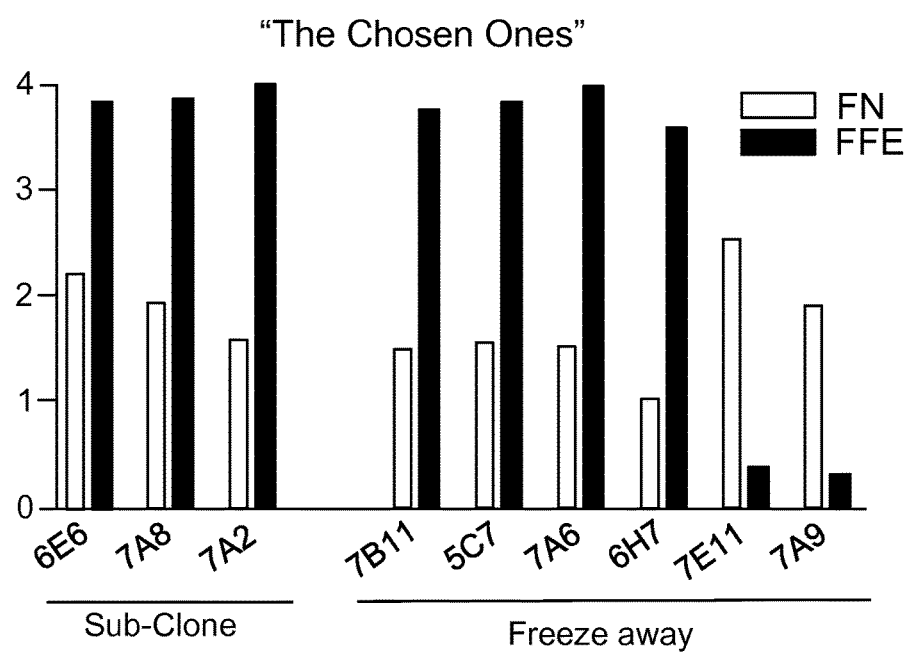
FIG. 6D is a bar graph showing ELISA results for FFE and fibronectin binding by monoclonal antibodies produced by the selected hybridoma clones from mouse 3.
Figure 7A:
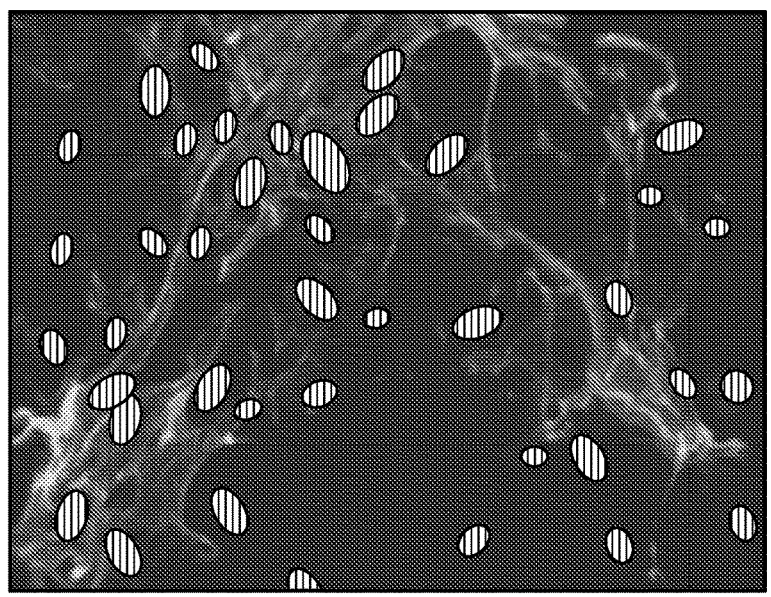
FIGS. 7A-7C are a set of immunofluorescence images of HUVEC showing that monoclonal antibodies produced by clones 6E7, 7A8, and 7A2 bind to an extracellular matrix protein, secreted by HUVEC (crosshatched regions indicate nuclei of HUVEC). The identity of the matrix protein was established by its reactivity with an antibody that binds human fibronectin.
Figure 7B:
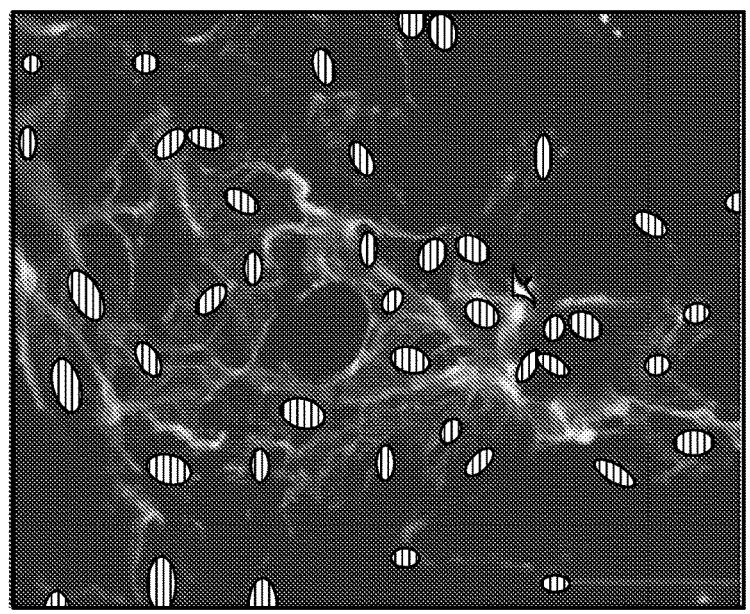
Figure 7C:
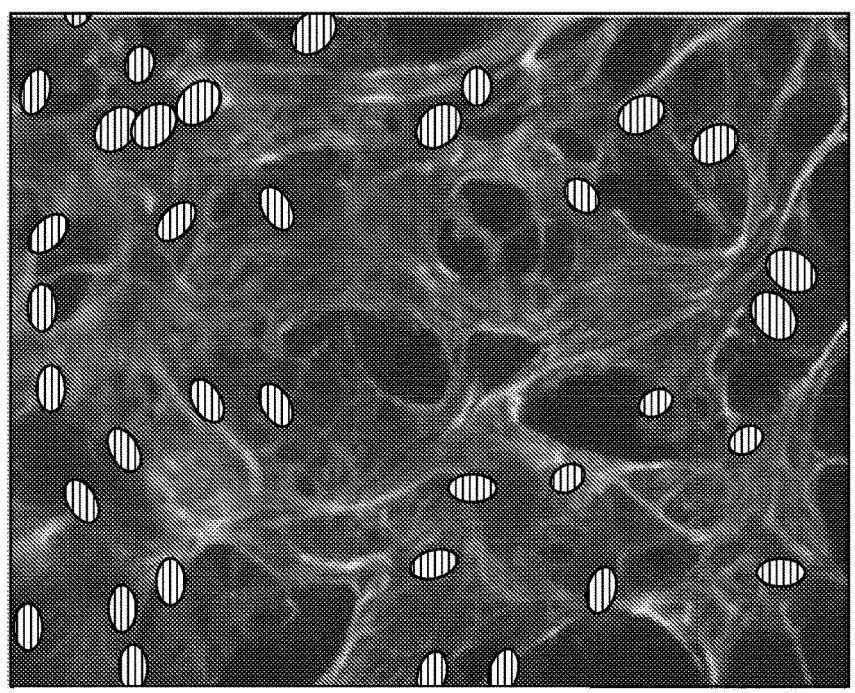

Tissue culture supernatant of the fused hybridoma clones was screened for binding to fibronectin and FFE. Twenty-four positive parental hybridoma clones were obtained. FIG. 6D shows the ELISA results for FFE and fibronectin binding by monoclonal antibodies produced by some of the 24 parental hybridoma clones. Among these, three clones (6E7, 7A8, 7A2) were chosen for sub-cloning and several other clones (7B11, 5C7, 7A6, 6H7, 7E11, and 7A9) were frozen away. After two rounds of sub-cloning, clones 6E7, 7A8, 7A2 became 96%, 94%, and 100% positive for fibronectin binding respectively and also bound to a similar extent to FFE. FIG. 7 shows all three monoclonal antibodies produced by clones 6E7, 7A8, and 7A2 bind to an extracellular matrix protein secreted by human umbilical endothelial cells (HU-VEC), mimicking the binding property of the FFE/fibronectin polyclonal antibody. The identity of the matrix protein was established by its reactivity with an antibody to human fibronectin. Thus, hybridoma clones 6E7, 7A8, and 7A2 produce stable monoclonal antibodies that selectively and specifically bind to endothelial fibronectin, as well as plasma fibronectin used in the ELISA assays, and fibrinogen, and fibrin fragment E. These three hybridoma clones were deposited at the American Type Culture Collection (ATCC) and designated as PTA-120972 (6E7), PTA-120970 (7A2), and PTA-120971 (7A8).

The nucleotide and amino acid sequences of the heavy chain variable region ($V_H$) and the light chain variable region ($V_L$) of the monoclonal antibodies produced by these hybridomas were determined. FIGS. 8-13 show the nucleotide and amino acid sequences of $V_H$ and $V_L$ of the monoclonal antibodies produced by hybridoma PTA-120972, PTA-120970, or PTA-120971. The CDRs of the $V_H$ region are labeled as CDR-H1, CDR-H2, and CRD-H3; the CDRs of the $V_L$ region are labeled as CDR-L1, CDR-L2, and CRD-L3.

As shown in FIG. 8, the 6E7 monoclonal antibody produced by hybridoma PTA-120972 comprises a heavy chain variable region with an amino acid sequence of SEQ ID NO: 2, which contains CDR1 with an amino acid sequence of SEQ ID NO: 4, CDR2 with an amino acid sequence of SEQ ID NO: 6, and CDR3 with an amino acid sequence of SEQ ID NO: 8. FIG. 9 shows the "6E7" monoclonal antibody comprises a light chain variable region with an amino acid sequence of SEQ ID NO: 10, which contains CDR1 with an amino acid sequence of SEQ ID NO: 12, CDR2 with an amino acid sequence of SEQ ID NO: 14, and CDR3 with an amino acid sequence of SEQ ID NO: 16. The nucleotide and amino acid sequences of the CDRs of $V_H$ and $V_L$ domains of 6E7 are also shown in Table 1.

FIG. 10 shows the 7A2 monoclonal antibody produced by hybridoma PTA-120970 comprises a heavy chain variable region with an amino acid sequence of SEQ ID NO: 18, which contains CDR1 with an amino acid sequence of SEQ ID NO: 20, CDR2 with an amino acid sequence of SEQ ID NO: 22, and CDR3 with an amino acid sequence of SEQ ID NO: 24. FIG. 11 shows the "7A2" monoclonal antibody comprises a light chain variable region with an amino acid sequence of SEQ ID NO: 26, which contains CDR1 with an amino acid sequence of SEQ ID NO: 28, CDR2 with an amino acid sequence of SEQ ID NO: 30, and CDR3 with an amino acid sequence of SEQ ID NO: 32. The nucleotide and amino acid sequences of the CDRs of $V_H$ and $V_L$ domains of 7A2 are also shown in Table 2.

As shown in FIG. 12, the "7A8" monoclonal antibody produced by hybridoma PTA-120971 comprises a heavy chain variable region with an amino acid sequence of SEQ ID NO: 34, which contains CDR1 with an amino acid sequence of SEQ ID NO: 20, CDR2 with an amino acid sequence of SEQ ID NO: 22, and CDR3 with an amino acid sequence of SEQ ID NO: 24. FIG. 13 shows the "7A8" monoclonal antibody comprises a light chain variable region with an amino acid sequence of SEQ ID NO: 26, which contains CDR1 with an amino acid sequence of SEQ ID NO: 28, CDR2 with an amino acid sequence of SEQ ID NO: 30, and CDR3 with an amino acid sequence of SEQ ID NO: 32. The nucleotide and amino acid sequences of 7A8's CDRs are the identical to the 7A2's CDRs listed in Table 2.

Example 2. Characterization of Monoclonal Antibodies of Example 1

The binding affinity of the monoclonal antibodies 7A8 and 6E7 of Example 1 to fibronectin was studied. A Biacore 3000 Instrument equipped with CM-5 sensor chip was used for antibody binding kinetics analysis. Purified Fibronectin protein was obtained from BIOPUR AG (#10-50-1101, Lot # B130728.01). The monoclonal antibodies 7A8 and 6E7 as well as the fibronectin protein were diluted in HBS-EP running buffer for Biacore analysis. No buffer exchange was performed. Anti-mouse capture antibody was immobilized on the flow cell and then the 7A8 or 6E7 antibody was run through the flow cells followed by the fibronectin protein. A flow cell immobilized with anti-mouse capture antibody alone was used as reference lane. Antigen binding responses were simulated at various concentrations as shown in FIGS. 11A-11B and all responses were fit simultaneously to a 1:1 (Langmuir) binding interaction model.

Associations were monitored for about 3 minutes and dissociations were monitored for about 8 minutes. Two independent experiments were performed. In the first experiment, a wider range of fibronectin concentration (500 nM to 15 nM) was used to verify the binding and then the concentration range was narrowed down to about 100 nM to 20 nM in the second experiment. The association constant (Ka), dissociation constant (Kd), and binding affinity were calculated in each experiment. $Chi^2$ indicates the model used fits well.

As shown in FIGS. 11A-11B, strong binding of 7A8 antibody to fibronectin protein was observed, which confirms the specificity of the 7A8 antibody to fibronectin. Signal reached saturation above 125 nM in the first experiment (FIG. 11A). Binding affinity of the 7A8 antibody to fibronectin was successfully measured by 1:1 (Langmuir) binding interaction model using Biacore evaluation software; the Kd is about $2.8\ e^{-9}$ to about $7.26\ e^{-9}$ and the binding affinity to fibronectin is in the nanomolar range between about 2 nM and about 8 nM (FIGS. 11A-11B). The 6E7 antibody did not bind nearly as strongly to the fibronectin protein as the 7A8 antibody in this experiment.

Example 3. A Polyclonal Antibody Raised Against Human Fibrinogen, Purified on FFE-Bound Column and Cross-Reacts with Human Fibronectin Generation and Purification of the Polyclonal Antibody New Zealand white rabbits were hyper-immunized with highly purified human fibrinogen (Hyphen BioMed, Neuville-sur-Oise, France) through repetitive boosts over a 3-month period. Rabbits were then bled to obtain hyperimmune serum. Specific FFE-binding antibodies were purified by affinity chromatography on an FFE-bound Sepharose 4B column. FFE was prepared as described in Example 1. Rabbit antiserum was first adsorbed with human serum globulins to remove nonspecific antibodies before passage through the FFE-bound Sepharose 4B column. Only antibodies reactive with FFE were retained by the column. Following extensive washing, the FFE-bound antibodies were eluted with 0.25 M glycine buffer at pH 2.5 and collected on one tenth volume of glycine 1 M at pH 9.00 to neutralize the acidic pH. About 50 µg of FFE-binding antibodies were obtained per ml of antiserum. The FFE-binding polyclonal antibody was then dialyzed against physiological saline, aliquoted, and stored frozen until use.

Binding of the Polyclonal Antibody to Fibronectin

Human umbilical endothelial cells (HUVEC) were grown on uncoated glass coverslips. Before confluence, the HUVEC were fixed with 4% formaldehyde. Thereafter, they were stained with the following antibodies: anti-CD31 antibody (BD Biosciences Pharmingen) diluted 1:100 in PBS and 1% bovine serum albumin; the FFE-binding polyclonal antibody (10 mg/ml); or anti-fibrin fragment D-Dimer (anti-DD at 10 mg/ml, purchased from Abcam, Paris, France). The anti-CD31 antibody was given a green fluorescence tag, and the FFE-binding polyclonal antibody and anti-DD antibody were each given a red fluorescence tag. Cell nuclei were counterstained by DAPI (Invitrogen) and thus appeared blue in the images (FIG. 1).

CD31 is an endothelial cell surface protein, thus anti-CD31 antibody labeled the cell surface of HUVEC in green (FIG. 1). The FFE-binding polyclonal antibody, shown in red, binds to an extracellular matrix protein secreted by HUVEC, which was identified to be fibronectin by antibody staining (FIG. 1). The anti-DD antibody does not bind to HUVEC or the extracellular matrix (FIG. 1). Therefore, the rabbit polyclonal antibody that was raised against human fibrinogen and purified by an FFE affinity column, also bound strongly to fibronectin secreted by HUVEC. These findings suggest that an epitope on human fibrinogen, is antigenically similar to an epitope on human fibronectin.

Example 4. Effects of the New Monoclonal Antibody of Example 1 and the Polyclonal Antibody of Example 3 on HUVEC Tubule Formation Human umbilical vein endothelial cells (HUVEC) were cultured in endothelial cell growth medium-2 (EGM-2) MV medium (LONZA, Saint Beauzire, France) in flasks pre-coated with Type 1 rat tail collagen (50 µg/ml) (BD Biosciences), and incubated at 37° C. in a humidified incubator with 5% $CO_2$.

Flat-bottom twelve-well plates were pre-coated with cold Matrigel basement membrane (purchase from BD Biosciences, Le Pont de Claix, France) for 30 minutes at 37° C. HUVEC cells were plated into these pre-coated wells at a density of $2 \times 10^5$ cells/well and incubated for 24 hours in EGM-2. In some wells, the polyclonal antibody of Example 3 was added to the wells before incubation. HUVEC tubule formation was visualized by an optical microscope at regular intervals (e.g., 6, 8, and 24 hours after plating), and images were captured using a digital camera. The number of tubules formed, the total tubule length, the number of junctions, and the total area covered by tubules were determined using image analysis software (AngioSys, TCS Cellworks, Buckingham, UK).

Figure 2:
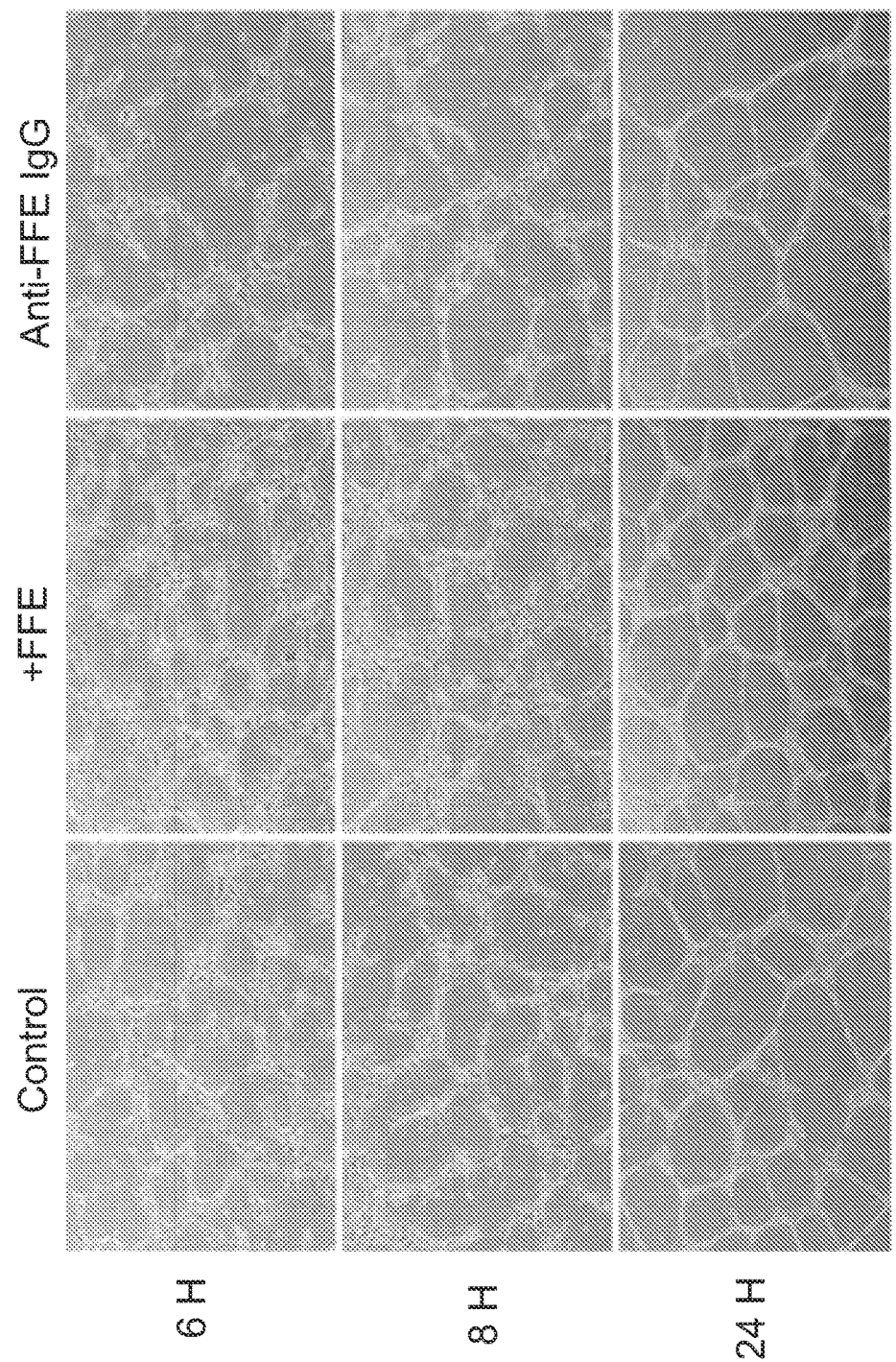
FIG. 2 is a set of related images of HUVEC on Matrigel showing that the rabbit polyclonal antibody that was raised against human fibrinogen and purified on immobilized FFE significantly (p=0.04-0.005) inhibits HUVEC tubule formation on Matrigel. Significance was calculated by image analysis software (AngioSys, TCS Cellworks, Buckingham, UK).

In the control wells with medium alone, HUVEC elongated and began to differentiate into tubules after 4 hours and tubule formation progressed over 6-24 hours (FIG. 2). The plate surface became maximally covered by tubule mesh in 8 hours; but the maximum number and length of tubules and the maximum number of tubule junctions were reached in 6 hours, remaining stable until 8 hours, after which they regress (FIG. 2). The polyclonal antibody of Example 3 significantly inhibits HUVEC tubule formation in Matrigel (FIG. 2).

As previously reported, various growth factors including epidermal growth factor (EGF), insulin-like growth factor 1, bovine fibroblast growth factor (bFGF), and platelet-derived growth factor (PDGF) exist in Matrigel (Vukicevic et al., Exp. Cell Res. 202:1, 1992). Thus, the polyclonal antibody of Example 3 inhibits HUVEC tubule formation in Matrigel by overcoming the promotion of angiogenesis by those growth factors.

In some wells of HUVEC culture, a new monoclonal antibody of Example 1, e.g., 6E7, 7A2, or 7A8, is added to the wells before incubation. HUVEC tubule formation is visualized by an optical microscope at the same time intervals (e.g., 6, 8, and 24 hours after plating), and images are captured using a digital camera. The number of tubules formed, the total tubule length, the number of junctions, and the total area covered by tubules are determined using image analysis software AngioSys.

Example 5. Effects of the New Monoclonal Antibody of Example 1 and the Polyclonal Antibody Against FFE and Fibronectin of Example 3 on Cell Proliferation An MTS assay was used to assess the effect of antibodies on HUVEC cell proliferation. MTS (3-(4,5-dimethylthiazol-2-yl)-5-(3-carboxymethoxyphenyl)-2-(4-sulfophenyl)-2H-tetrazolium), is reduced by intracellular dehydrogenases into a colored formazan product that is soluble in tissue culture medium. The amount of formazan produced is directly proportional to the number of living cells in culture and can be measured at 490-500 nm in phosphate-buffered saline.

On Day 1, HUVEC were plated onto 48-well tissue culture plates, at $10^4$ cells/well in endothelial cell growth medium-2 (EGM-2) without VEGF and bFGF for 3 hours. To achieve a range, HUVEC were seeded at two densities, $3 \times 10^4$ and $6 \times 10^4$ cells/well. Then HUVEC were cultured for 5 days in triplicate either in complete EGM-2 or EGM-2 without VEGF and bFGF; or in medium supplemented with the polyclonal antibody raised against fibrinogen and purified on FFE-bound column (2 µg/mL). On Day 1 (after 2 h), Day 3 and Day 5, cells were washed twice with PBS, and the medium was replaced with fresh medium (170 µL) and MTS reagent (30 µL). The plate was incubated (37° C.) for 2 hours. Two aliquots (100 µL) of medium from each well were transferred to a 96-well tissue plate and the absorbance (490 nm) was recorded. Finally, HUVEC were washed twice and cultured in their suitable medium. Paired student's t-test was used to compare different culture conditions.

Figure 3A:
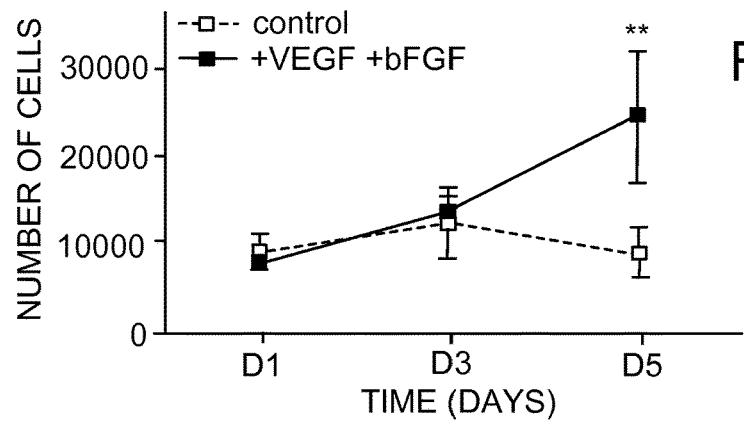
FIG. 3A is a line graph showing that HUVEC proliferation was significantly promoted by the addition of VEGF and bFGF.
Figure 3B:
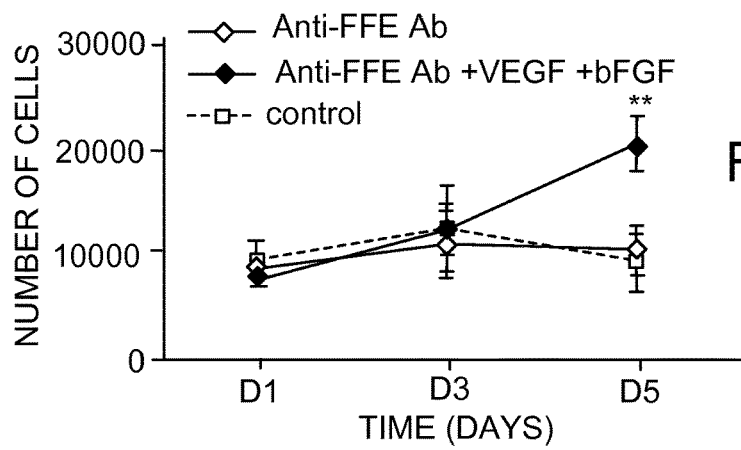
FIG. 3B is a line graph showing that the rabbit polyclonal antibody that was raised against human fibrinogen and purified on FFE-bound column had no effect on cell proliferation.

HUVEC cultured in medium without VEGF and bFGF maintained a level of basal proliferation, which was significantly (p=0.002) promoted by the addition of VEGF and bFGF as measured on Day 3 and Day 5 (FIG. 3A). By contrast, the polyclonal antibody of Example 3 had no effect on cell proliferation (FIG. 3B).

HUVEC are also cultured for 5 days in medium supplemented with the new monoclonal antibody, e.g., 6E7, 7A2, or 7A8. On Day 1 (after 2 h), Day 3 and Day 5, cells are washed twice with PBS, and the medium is replaced with fresh medium (170 µL) and MTS reagent (30 µL). The plate is incubated (37° C.) for 2 hours. Two aliquots (100 µL) of medium from each well are transferred to a 96-well tissue plate and the absorbance (490 nm) is recorded. Finally, HUVEC are washed twice and cultured in their suitable medium. Paired student's t-test is used to compare different culture conditions.

These findings indicate that the FFE/fibronectin antibody had no effect on cell proliferation, and thus acts independent of the angiogenic growth factors. A combination of the corresponding new monoclonal antibody and an inhibitor of the angiogenic growth factor, e.g., an anti-VEGF antibody, may have an additive or synergistic effect.

Example 6. The Effect of the New Monoclonal Antibody of Example 1 and the Polyclonal Antibody of Example 3 on Tumor Growth and Angiogenesis Human Colon Adenocarcinoma Xenograft Mouse Model Eight week old NOD/SCID mice were maintained under pathogen-free conditions and used in all in vivo experiments. Human colon adenocarcinoma cell line (HT29) was obtained from the American Type Culture Collection (LGC-Promotech, Nancy, France). NOD/SCID mice were injected subcutaneously with $2 \times 10^5$ HT29 cells, and develop visible tumors after one week. The length and width of the tumors were measured once a week with a caliper, and the volumes of the tumors are calculated using the following formula: volume=(width$^2 \times$length)/2. The tumor weight and volume at autopsy were measured and compared with the calculated volume. All mice were sacrificed when the size of the tumor becomes too burdensome or at 43 days after HT29 injection.

Antibody Treatment

Figure 4:
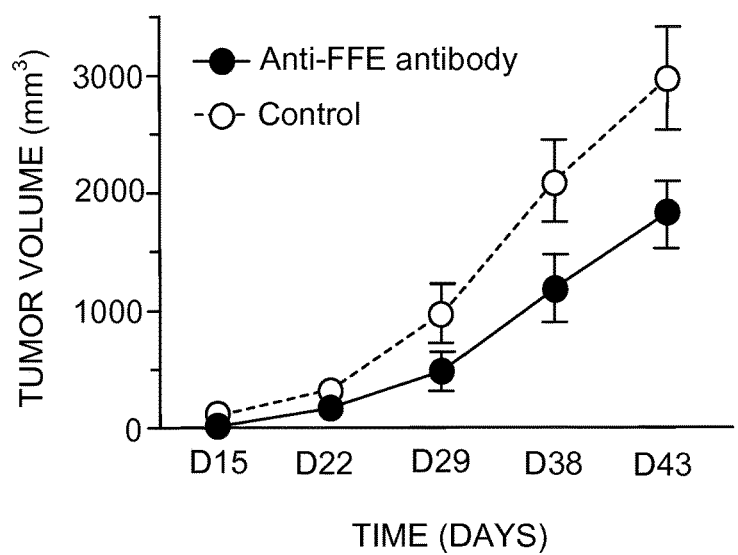
FIG. 4 is a line graph showing the inhibition of tumor growth by the rabbit polyclonal antibody that was raised against human fibrinogen and purified on FFE-bound column. Significant (p<0.001) inhibition of tumor growth (solid line) by the polyclonal antibody occurred from Day 15 through Day 43 when compared to the control PBS-treated mice (dashed line).

Mice bearing tumors were divided into an experimental group and a control group. Under anesthesia, mice in the experimental groups were injected with the polyclonal FFE/fibronectin antibody of Example 2 directly under the tumor mass on Days 6, 15, 22 and 29. Mice in the control group were injected with an equal volume of PBS at the same site and time intervals. Tumor volumes (mm$^3$) were measured and plotted against time after treatment. Statistical analysis of differences in tumor volumes was performed using Fisher test (Two way ANOVA comparison). Tumors from mice treated with the polyclonal antibody of Example 3 were significantly smaller than those from the control mice at all time points measured from day 15 on (FIG. 4).

Similarly, mice bearing tumors are divided into another experimental group and a control group. Under anesthesia, mice in the experimental groups are injected with the new monoclonal antibody of Example 1, e.g., 6E7, 7A2, or 7A8, directly under the tumor mass on Days 6, 15, 22 and 29. Mice in the control group are injected with an equal volume of PBS at the same site and time intervals. Tumor volumes (mm$^3$) are measured and plotted against time after treatment. Statistical analysis of differences in tumor volumes is performed using Fisher test (Two way ANOVA comparison).

Histological Analysis of Tumor Angiogenesis

Tumors from the control mice and the polyclonal FFE/fibronectin antibody-treated mice were embedded in tissue freezing medium and frozen at −80° C. Cryostat sections (7 μm) of the tumors were air-dried at room temperature and rehydrated in PBS. Sections were fixed in cold acetone for 15 minutes, washed with PBS, and then incubated for 1 hour at room temperature with blocking solution (kit MOM, AbCys, Paris, France) to block nonspecific sites. Next, the slides were washed with PBS and incubated at room temperature for more than 30 minutes with the specific rat anti-mouse CD31 antibody (BD Biosciences Pharmingen) diluted 1:50 with PBS and 1% bovine serum albumin. After reacting with a secondary antibody (goat anti-rat Alexa Fluor 488, Invitrogen Molecular Probes, Cergy Pontoise, France) for 30 minutes in the dark, the sections were processed with glycergel mounting medium (DAKO, Trappes, France) and DAPI (Invitrogen) according to the manufacturer's instructions. Immunofluorescence was visualized with a fluorescence microscope (100× magnifications), and images were captured with a Leica camera coupled with an image Software (Metaview). Tissue slices directly preceding and following the one used for immunofluorescent staining were stained with hematoxylin, eosin, and safran, and viewed under an optic microscope (100× magnifications).

Figure 5A:
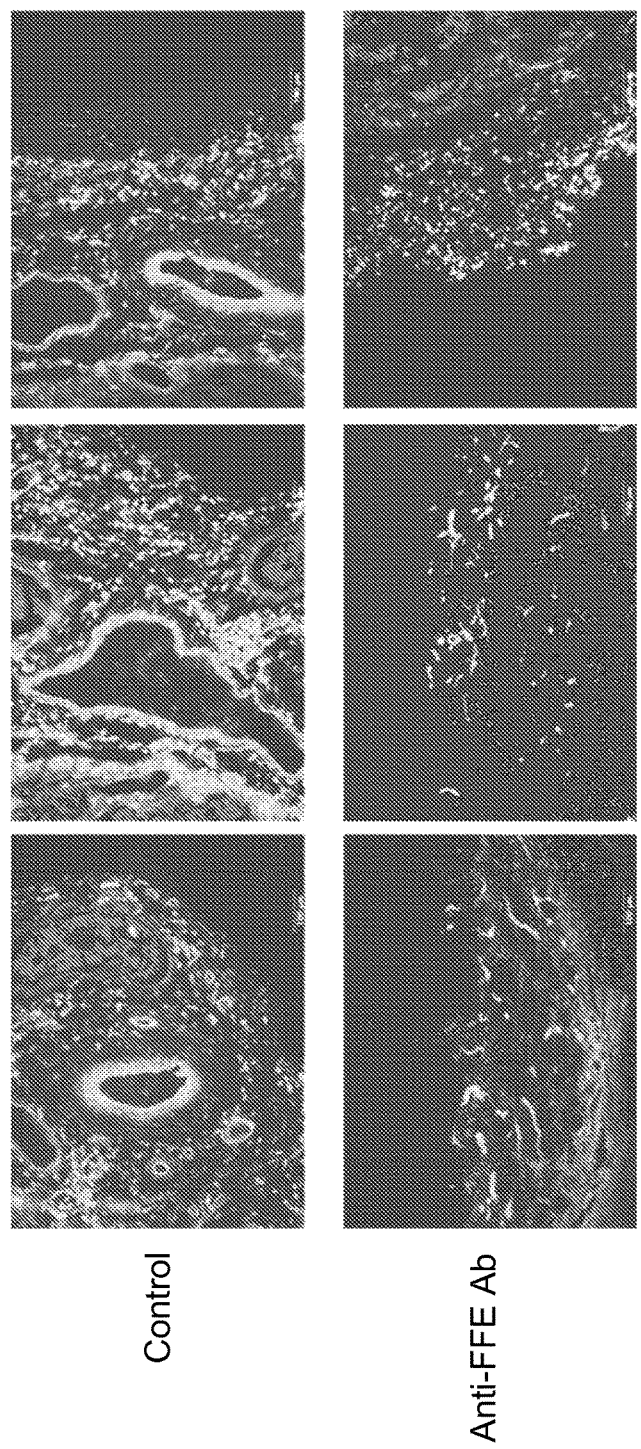
FIGS. 5A and 5B are two sets of immunofluorescence (5A) and histologic (5B) images showing the complete suppression of angiogenesis by the rabbit polyclonal antibody that was raised against human fibrinogen and purified on FFE-bound column. Labeling endothelium with an anti-CD31 antibody (5A) and Hematoxylin & Eosin staining of adjacent sections (5B) both showed that in the untreated control mice, numerous well-formed vessels exist at the tumor periphery illustrating tumor angiogenesis. By contrast, only small vessel fragments and no formed vessels were found in the tumor periphery in all the mice treated with the polyclonal antibody raised against fibrinogen and purified on FFE-bound column.
Figure 5B:
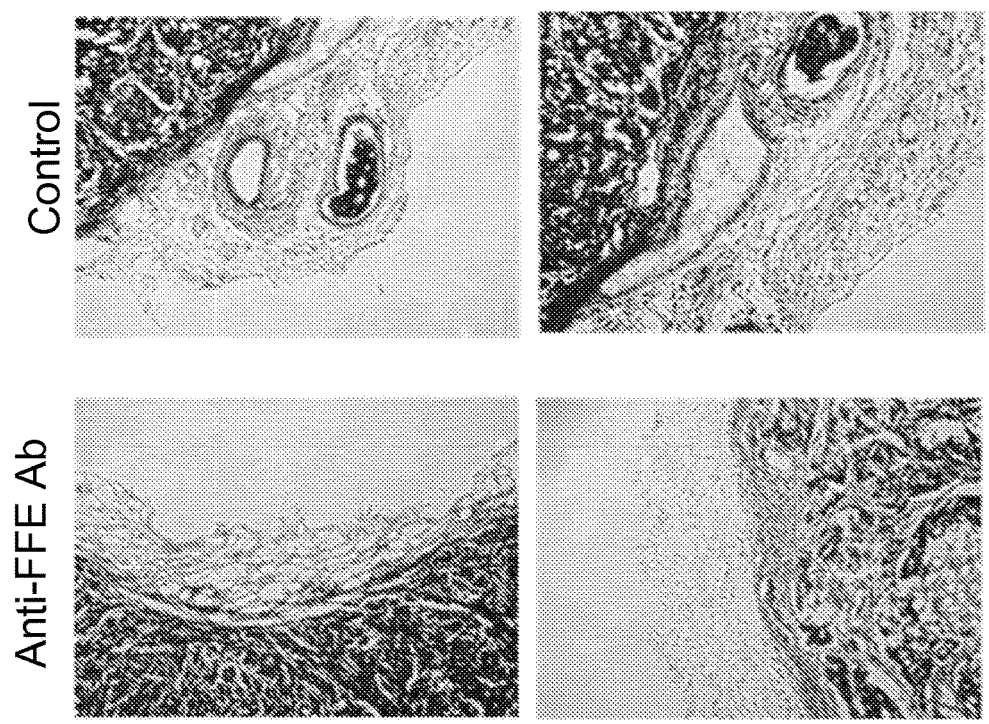

Three different tumors from the control group and three different tumors from the antibody-treated group were analyzed. Nine different cryosections were examined in each tumor. For each tumor, sections of the tumor periphery, showing the interface with normal tissue, and sections of the middle of the tumor were examined. Proliferation of vessels was seen in control mice consistent with angiogenesis at the advancing edge of the tumor (FIG. 5). By contrast, no vessels and only residual CD 31-staining endothelial vessel fragments were visible at the tumor periphery in all antibody-treated mice (FIG. 5). Sections of the tumor center from either the control mice or the antibody-treated mice showed only tissue necrosis with no vascularization (data not shown). These findings show that the antibody had an unusually potent anti-angiogenic effect.

Tumor sections from the new monoclonal antibody-treated mice are processed and examined in the same manner as described above. Three different tumors and nine different cryosections of each tumor are examined. For each tumor, sections of the tumor periphery, showing the interface with normal tissue, and sections of the middle of the tumor are examined.

As discussed in Examples 3-4, the anti-angiogenic effect of these antibodies is independent of the vascular endothelial growth factor (VEGF). VEGF inhibitors, e.g., anti-VEGF antibody or anti-VEGF aptamer, have dominated anti-angiogenic therapies up till now. Since the new monoclonal antibody, like the FFE/fibronectin polyclonal, is not directed against VEGF or other growth factor, the same toxic effects seen in anti-VEGF therapies will not occur. These findings suggest that the new monoclonal antibody alone, or in combination with a complementary anti-angiogenesis inhibitor, e.g., a VEGF inhibitor, can greatly improve currently available anti-angiogenic therapies.

DEPOSIT STATEMENT

The subject cultures have been deposited under conditions that assure that access to the cultures will be available during the pendency of the patent application disclosing them to one determined by the Commissioner of Patents and Trademarks to be entitled thereto under 37 C.F.R. 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30

(thirty) years after the date of deposit or for the enforceable life of any patent which may issue disclosing the cultures plus five years after the last request for a sample from the deposit. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated monoclonal antibody or antigen-binding fragment thereof that (1) binds to human fibronectin, human fibrinogen, and fibrin fragment E, and (2) is produced by the hybridoma deposited at the American Type Culture Collection (ATCC) and designated as PTA-120972.

2. An isolated monoclonal antibody or antigen-binding fragment thereof that binds to human fibronectin, human fibrinogen, and fibrin fragment E and comprises a heavy chain CDR1, a heavy chain CDR2, a heavy chain CDR3, a light chain CDR1, a light chain CDR2, and a light chain CDR3 wherein:
   (i) the heavy chain CDR1 comprises the amino acid sequence of SEQ ID NO:20,
   (ii) the heavy chain CDR2 comprises the amino acid sequence of SEQ ID NO:22,
   (iii) the heavy chain CDR3 comprises the amino acid sequence of SEQ ID NO:24,
   (iv) the light chain CDR1 comprises the amino acid sequence of SEQ ID NO:28,
   (v) the light chain CDR2 comprises the amino acid sequence of SEQ ID NO:30, and
   (vi) the light chain CDR3 comprises the amino acid sequence of SEQ ID NO:32.

3. The isolated monoclonal antibody or antigen-binding fragment thereof of claim 1, wherein the isolated monoclonal antibody or antigen-binding fragment thereof is a humanized antibody.

4. The isolated monoclonal antibody or antigen-binding fragment thereof of claim 1, wherein the isolated monoclonal antibody or antigen-binding fragment thereof is a fully human antibody.

5. The isolated monoclonal antibody or antigen-binding fragment thereof of claim 1, wherein the isolated monoclonal antibody or antigen-binding fragment has an anti-angiogenic effect, but does not inhibit endothelial cell proliferation.

6. The antigen-binding fragment of claim 1, wherein the antigen-binding fragment is selected from the group consisting of a Fab fragment, a F(ab')2 fragment, a scFv fragment, and a sc(Fv)2 diabody.

7. A composition comprising at least one isolated monoclonal antibody or antigen-binding fragment of claim 1.

8. The composition of claim 7, further comprising one or more angiogenesis inhibitors selected from the group consisting of bevacizumab, sorafenib, sunitinib, pazopanib, axitinib, cabozantinib, regorafenib, vandetanib, temsirolimus, everolimus, lenalidomide, erlotinib, angiostatin, endostatin, tumstatin, canstatin, restin, and arresten.

9. The composition of claim 7, further comprising a chemotherapeutic agent.

10. A composition comprising at least one isolated monoclonal antibody or antigen-binding fragment of claim 2.

11. The isolated monoclonal antibody or antigen-binding fragment thereof of claim 2, wherein the isolated monoclonal antibody or antigen-binding fragment thereof is a humanized antibody.

12. The isolated monoclonal antibody or antigen-binding fragment thereof of claim 2, wherein the isolated monoclonal antibody or antigen-binding fragment thereof is a fully human antibody.

13. The composition of claim 8, wherein the angiogenesis inhibitor comprises bevacizumab.

14. An isolated monoclonal antibody or antigen-binding fragment thereof that binds to human fibronectin, human fibrinogen, and fibrin fragment E and comprises a heavy chain CDR1, a heavy chain CDR2, and a heavy chain CDR3, a light chain CDR1, a light chain CDR2, and a light chain CDR3, wherein:
   (i) the heavy chain CDR1 comprises the amino acid sequence of SEQ ID NO:4,
   (ii) the heavy chain CDR2 comprises the amino acid sequence of SEQ ID NO:6,
   (iii) the heavy chain CDR3 comprises the amino acid sequence of SEQ ID NO:8,
   (iv) the light chain CDR1 comprises the amino acid sequence of SEQ ID NO:12,
   (v) the light chain CDR2 comprises the amino acid sequence of SEQ ID NO:14, and
   (vi) the light chain CDR3 comprises the amino acid sequence of SEQ ID NO:16.

15. The isolated monoclonal antibody or antigen-binding fragment thereof of claim 14, wherein the isolated monoclonal antibody or antigen-binding fragment thereof is a humanized antibody.

16. The isolated monoclonal antibody or antigen-binding fragment thereof of claim 14, wherein the isolated monoclonal antibody or antigen-binding fragment thereof is a fully human antibody.

17. The antigen-binding fragment of claim 14, wherein the antigen-binding fragment is selected from the group consisting of a Fab fragment, a F(ab')2 fragment, a scFv fragment, and a sc(Fv)2 diabody.

18. A composition comprising at least one isolated monoclonal antibody or antigen-binding fragment of claim 14.

19. The composition of claim 18, further comprising one or more angiogenesis inhibitors selected from the group consisting of bevacizumab, sorafenib, sunitinib, pazopanib, axitinib, cabozantinib, regorafenib, vandetanib, temsirolimus, everolimus, lenalidomide, erlotinib, angiostatin, endostatin, tumstatin, canstatin, restin, and arresten.

20. The composition of claim 19, wherein the angiogenesis inhibitor comprises bevacizumab.

21. The composition of claim 18, further comprising a chemotherapeutic agent.

22. The composition of claim 19, further comprising a chemotherapeutic agent.

23. A method of inhibiting an angiogenesis-related disorder in a subject, the method comprising administering to the subject an isolated monoclonal antibody or antigen-binding fragment thereof of claim 1, wherein the angiogenesis-related disorder is a solid tumor.

* * * * *

SEQUENCE LISTING

```
<160> NUMBER OF SEQ ID NOS: 42

<210> SEQ ID NO 1
<211> LENGTH: 364
<212> TYPE: DNA
<213> ORGANISM: Mus musculus

<400> SEQUENCE: 1
caggtccaac tgcagcagcc tgggtctgtg ctggtgaggc cgggagcttc agtgaaactg      60
tcctgcaagg cttctggcta caccttcacc agctactgga tgcactgggc gaagcagagg     120
cctggacaag gccttgagtg gattggacag attcatccta ttagtggtaa tattaagtac     180
aatgagaagt tcaagggcaa ggccacactg actgtagaca catctcccag cacagcctac     240
gtggatctca gcagcctgac atctgaggac tctgcggtct attactgtgc aagagatact     300
tactatacta ataacgatgc tgtggactac tggggtcaag gaacctcagt caccgtctcc     360
tcag                                                                 364

<210> SEQ ID NO 2
<211> LENGTH: 121
<212> TYPE: PRT
<213> ORGANISM: Mus musculus

<400> SEQUENCE: 2

Gln Val Gln Leu Gln Gln Pro Gly Ser Val Leu Val Arg Pro Gly Ala
 1               5                  10                  15

Ser Val Lys Leu Ser Cys Lys Ala Ser Gly Tyr Thr Phe Thr Ser Tyr
            20                  25                  30

Trp Met His Trp Ala Lys Gln Arg Pro Gly Gln Gly Leu Glu Trp Ile
        35                  40                  45

Gly Gln Ile His Pro Ile Ser Gly Asn Ile Lys Tyr Asn Glu Lys Phe
    50                  55                  60

Lys Gly Lys Ala Thr Leu Thr Val Asp Thr Ser Pro Ser Thr Ala Tyr
65                  70                  75                  80

Val Asp Leu Ser Ser Leu Thr Ser Glu Asp Ser Ala Val Tyr Tyr Cys
                85                  90                  95

Ala Arg Asp Thr Tyr Tyr Thr Asn Asn Asp Ala Val Asp Tyr Trp Gly
            100                 105                 110

Gln Gly Thr Ser Val Thr Val Ser Ser
        115                 120

<210> SEQ ID NO 3
<211> LENGTH: 30
<212> TYPE: DNA
<213> ORGANISM: Mus musculus

<400> SEQUENCE: 3
ggctacacct tcaccagcta ctggatgcac                                      30
```

<210> SEQ ID NO 4
<211> LENGTH: 10
<212> TYPE: PRT
<213> ORGANISM: Mus musculus

<400> SEQUENCE: 4

Gly Tyr Thr Phe Thr Ser Tyr Trp Met His
1               5                   10

<210> SEQ ID NO 5
<211> LENGTH: 51
<212> TYPE: DNA
<213> ORGANISM: Mus musculus

<400> SEQUENCE: 5
cagattcatc ctattagtgg taatattaag tacaatgaga agttcaaggg c            51

<210> SEQ ID NO 6
<211> LENGTH: 17
<212> TYPE: PRT
<213> ORGANISM: Mus musculus

<400> SEQUENCE: 6

Gln Ile His Pro Ile Ser Gly Asn Ile Lys Tyr Asn Glu Lys Phe Lys
1               5                   10                  15

Gly

<210> SEQ ID NO 7
<211> LENGTH: 36
<212> TYPE: DNA
<213> ORGANISM: Mus musculus

<400> SEQUENCE: 7
gatacttact atactaataa cgatgctgtg gactac                             36

<210> SEQ ID NO 8
<211> LENGTH: 12
<212> TYPE: PRT
<213> ORGANISM: Mus musculus

<400> SEQUENCE: 8

Asp Thr Tyr Tyr Thr Asn Asn Asp Ala Val Asp Tyr
1               5                   10

<210> SEQ ID NO 9
<211> LENGTH: 322
<212> TYPE: DNA
<213> ORGANISM: Mus musculus

<400> SEQUENCE: 9
gacattgtga tgacccagtc tcacaaattc atgtccacat cagtaggaga cagggtcagc      60
atcacctgca aggccagtca ggatgtgggt agtgttgtag cctggtatca acagaaacca     120
ggacaatctc ctaaactact gatttactgg gcatccaccc ggcatactgg aatccctaat     180
cgcttcacag gcaggggatc tgggacagat ttcactctca ccattaccaa tgtgcagtct     240
gaagacttgg cagattattt ctgtcagcaa tatagcaact atcctctcac gttcggtgct     300
gggaccaagc tggagctgaa ac                                             322

<210> SEQ ID NO 10
<211> LENGTH: 107
<212> TYPE: PRT
<213> ORGANISM: Mus musculus

<400> SEQUENCE: 10

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ser Val
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Ile Pro Asn Arg Phe Thr Gly
50                  55                  60

Arg Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Ser Asn Tyr Pro Leu
                85                  90                  95

Thr Phe Gly Ala Gly Thr Lys Leu Glu Leu Lys
            100                 105

<210> SEQ ID NO 11
<211> LENGTH: 33
<212> TYPE: DNA
<213> ORGANISM: Mus musculus

<400> SEQUENCE: 11
aaggccagtc aggatgtggg tagtgttgta gcc                         33

<210> SEQ ID NO 12
<211> LENGTH: 11
<212> TYPE: PRT
<213> ORGANISM: Mus musculus

<400> SEQUENCE: 12

Lys Ala Ser Gln Asp Val Gly Ser Val Val Ala
1               5                   10

<210> SEQ ID NO 13
<211> LENGTH: 21
<212> TYPE: DNA
<213> ORGANISM: Mus musculus

<400> SEQUENCE: 13
tgggcatcca cccggcatac t                                      21

<210> SEQ ID NO 14
<211> LENGTH: 7
<212> TYPE: PRT
<213> ORGANISM: Mus musculus

<400> SEQUENCE: 14

Trp Ala Ser Thr Arg His Thr
1               5

<210> SEQ ID NO 15
<211> LENGTH: 27
<212> TYPE: DNA
<213> ORGANISM: Mus musculus

<400> SEQUENCE: 15
cagcaatata gcaactatcc tctcacg                                27

<210> SEQ ID NO 16
<211> LENGTH: 9
<212> TYPE: PRT
<213> ORGANISM: Mus musculus

<400> SEQUENCE: 16

Gln Gln Tyr Ser Asn Tyr Pro Leu Thr
 1               5

<210> SEQ ID NO 17
<211> LENGTH: 355
<212> TYPE: DNA
<213> ORGANISM: Mus musculus

<400> SEQUENCE: 17
caggtgcagc tgagggagtc agaacctggc ctggtggcgc cctcacagag cctgtccatc      60
acatgcactg tctctgggtt ctcattaacc agctatgctg taagctgggt tcgccagcca     120
ccaggcaagg gtctggagtg gcttggagta atatggactg gtggaggcac aaattataat     180
tcagctctca atccagact gagcatcagc agagacaact ccaagaatca gttttctta      240 aaaatgaaca gtctgcaaac tgatgacaca gccaggtact actgtgccag atatagtaac     300
ctttactatg ctatggacta ctggggtcaa ggaacctcag tcaccgtctc ctcag          355

<210> SEQ ID NO 18
<211> LENGTH: 118
<212> TYPE: PRT
<213> ORGANISM: Mus musculus

<400> SEQUENCE: 18

Gln Val Gln Leu Arg Glu Ser Glu Pro Gly Leu Val Ala Pro Ser Gln
 1               5                  10                  15

Ser Leu Ser Ile Thr Cys Thr Val Ser Gly Phe Ser Leu Thr Ser Tyr
                20                  25                  30

Ala Val Ser Trp Val Arg Gln Pro Pro Gly Lys Gly Leu Glu Trp Leu
            35                  40                  45

Gly Val Ile Trp Thr Gly Gly Gly Thr Asn Tyr Asn Ser Ala Leu Lys
        50                  55                  60

Ser Arg Leu Ser Ile Ser Arg Asp Asn Ser Lys Asn Gln Val Phe Leu
65                  70                  75                  80

Lys Met Asn Ser Leu Gln Thr Asp Asp Thr Ala Arg Tyr Tyr Cys Ala
                85                  90                  95

Arg Tyr Ser Asn Leu Tyr Tyr Ala Met Asp Tyr Trp Gly Gln Gly Thr
                100                 105                 110

Ser Val Thr Val Ser Ser
        115

<210> SEQ ID NO 19
<211> LENGTH: 30
<212> TYPE: DNA
<213> ORGANISM: Mus musculus

<400> SEQUENCE: 19
gggttctcat taaccagcta tgctgtaagc                                        30

<210> SEQ ID NO 20
<211> LENGTH: 10
<212> TYPE: PRT
<213> ORGANISM: Mus musculus

<400> SEQUENCE: 20

Gly Phe Ser Leu Thr Ser Tyr Ala Val Ser
1               5                   10

<210> SEQ ID NO 21
<211> LENGTH: 48
<212> TYPE: DNA
<213> ORGANISM: Mus musculus

<400> SEQUENCE: 21
gtaatatgga ctggtggagg cacaaattat aattcagctc tcaaatcc            48

<210> SEQ ID NO 22
<211> LENGTH: 16
<212> TYPE: PRT
<213> ORGANISM: Mus musculus

<400> SEQUENCE: 22

Val Ile Trp Thr Gly Gly Thr Asn Tyr Asn Ser Ala Leu Lys Ser
1               5                   10                  15

<210> SEQ ID NO 23
<211> LENGTH: 30
<212> TYPE: DNA
<213> ORGANISM: Mus musculus

<400> SEQUENCE: 23
tatagtaacc tttactatgc tatggactac                               30

<210> SEQ ID NO 24
<211> LENGTH: 10
<212> TYPE: PRT
<213> ORGANISM: Mus musculus

<400> SEQUENCE: 24

Tyr Ser Asn Leu Tyr Tyr Ala Met Asp Tyr
1               5                   10

<210> SEQ ID NO 25
<211> LENGTH: 322
<212> TYPE: DNA
<213> ORGANISM: Mus musculus

<400> SEQUENCE: 25
gacattgtga tgacccagtc tcaaaaattc atgtccacat cagtaggaga gagggtcagc    60
atcacctgca aggccagtca gaatgtaggt actaatgttg cctggtatca gcagaaagca    120
gggcagtctc ttgaactgct gatctatggg gcatccaacc ggcacactgg agtccctgat    180
cgcttcacag gcagtggatc tgggacagat ttcaccctca ccatcaccaa tgtgcagtct    240
gaagacatga caaattattt ctgtgaacaa tataggagct atcctctgac gttcggtgga    300
ggcagcaagc tggaaatcaa ac                                           322

<210> SEQ ID NO 26
<211> LENGTH: 107
<212> TYPE: PRT
<213> ORGANISM: Mus musculus

<400> SEQUENCE: 26

Asp Ile Val Met Thr Gln Ser Gln Lys Phe Met Ser Thr Ser Val Gly
1               5                   10                  15

Glu Arg Val Ser Ile Thr Cys Lys Ala Ser Gln Asn Val Gly Thr Asn
            20                  25                  30

Val Ala Trp Tyr Gln Gln Lys Ala Gly Gln Ser Leu Glu Leu Leu Ile
        35                  40                  45

Tyr Gly Ala Ser Asn Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Met Thr Asn Tyr Phe Cys Gln Gln Tyr Arg Ser Tyr Pro Leu
                85                  90                  95

Thr Phe Gly Gly Gly Ser Lys Leu Glu Ile Lys
            100                 105

<210> SEQ ID NO 27
<211> LENGTH: 33
<212> TYPE: DNA
<213> ORGANISM: Mus musculus

<400> SEQUENCE: 27
aaggccagtc agaatgtagg tactaatgtt gcc                                33

<210> SEQ ID NO 28
<211> LENGTH: 11
<212> TYPE: PRT
<213> ORGANISM: Mus musculus

<400> SEQUENCE: 28

Lys Ala Ser Gln Asn Val Gly Thr Asn Val Ala
1               5                   10

<210> SEQ ID NO 29
<211> LENGTH: 21
<212> TYPE: DNA
<213> ORGANISM: Mus musculus

<400> SEQUENCE: 29
ggggcatcca accggcacac t                                             21

<210> SEQ ID NO 30
<211> LENGTH: 7
<212> TYPE: PRT
<213> ORGANISM: Mus musculus

<400> SEQUENCE: 30

Gly Ala Ser Asn Arg His Thr
1               5

<210> SEQ ID NO 31
<211> LENGTH: 27
<212> TYPE: DNA
<213> ORGANISM: Mus musculus

<400> SEQUENCE: 31
gaacaatata ggagctatcc tctgacg                                       27

<210> SEQ ID NO 32
<211> LENGTH: 9
<212> TYPE: PRT
<213> ORGANISM: Mus musculus

<400> SEQUENCE: 32

Glu Gln Tyr Arg Ser Tyr Pro Leu Thr
 1               5

<210> SEQ ID NO 33
<211> LENGTH: 355
<212> TYPE: DNA
<213> ORGANISM: Mus musculus

<400> SEQUENCE: 33
caggtgcagc tgagggagtc agaacctggc ctggtggcgc cctcacggag cctgtccatc     60
acatgcactg tctctgggtt ctcattaacc agctatgctg taagctgggt tcgccagcca    120
ccaggcaagg gtctggagtg gcttggagta atatggactg gtggaggcac aaattataat    180
tcagctctca atccagact gagcatcagc aaagacaact ccaagaatca agttttctta    240
aaaatgaaca gtctgcaaac tgatgacaca gccaggtact actgtgccag atatagtaac    300
ctttactatg ctatggacta ctggggtcaa ggaacctcag tcaccgtctc ctcag         355

<210> SEQ ID NO 34
<211> LENGTH: 118
<212> TYPE: PRT
<213> ORGANISM: Mus musculus

<400> SEQUENCE: 34

Gln Val Gln Leu Arg Glu Ser Glu Pro Gly Leu Val Ala Pro Ser Arg
 1               5                  10                  15

Ser Leu Ser Ile Thr Cys Thr Val Ser Gly Phe Ser Leu Thr Ser Tyr
                20                  25                  30

Ala Val Ser Trp Val Arg Gln Pro Pro Gly Lys Gly Leu Glu Trp Leu
            35                  40                  45

Gly Val Ile Trp Thr Gly Gly Gly Thr Asn Tyr Asn Ser Ala Leu Lys
        50                  55                  60

Ser Arg Leu Ser Ile Ser Lys Asp Asn Ser Lys Asn Gln Val Phe Leu
65                  70                  75                  80

Lys Met Asn Ser Leu Gln Thr Asp Asp Thr Ala Arg Tyr Tyr Cys Ala
                85                  90                  95

Arg Tyr Ser Asn Leu Tyr Tyr Ala Met Asp Tyr Trp Gly Gln Gly Thr
            100                 105                 110

Ser Val Thr Val Ser Ser
        115

<210> SEQ ID NO 35
<211> LENGTH: 211
<212> TYPE: PRT
<213> ORGANISM: Homo sapiens

<400> SEQUENCE: 35

Met Gln Asn Gly Ala Gly Ala Ser Arg Thr Ser Thr Ile Phe Leu Asn
 1               5                  10                  15

Gly Asn Arg Glu Arg Pro Leu Asn Val Phe Cys Asp Met Glu Thr Asp
                20                  25                  30

Gly Gly Gly Trp Leu Val Phe Gln Arg Arg Met Asp Gly Gln Thr Asp
            35                  40                  45

Phe Trp Arg Asp Trp Glu Asp Tyr Ala His Gly Phe Gly Asn Ile Ser
    50                  55                  60

Gly Glu Phe Trp Leu Gly Asn Glu Ala Leu His Ser Leu Thr Gln Ala
 65              70                  75                  80

Gly Asp Tyr Ser Ile Arg Val Asp Leu Arg Ala Gly Asp Glu Ala Val
                 85                  90                  95

Phe Ala Gln Tyr Asp Ser Phe His Val Asp Ser Ala Ala Glu Tyr Tyr
                100                 105                 110

Arg Leu His Leu Glu Gly Tyr His Gly Thr Ala Gly Asp Ser Met Ser
            115                 120                 125

Tyr His Ser Gly Ser Val Phe Ser Ala Arg Asp Arg Asp Pro Asn Ser
        130                 135                 140

Leu Leu Ile Ser Cys Ala Val Ser Tyr Arg Gly Ala Trp Trp Tyr Arg
145                 150                 155                 160

Asn Cys His Tyr Ala Asn Leu Asn Gly Leu Tyr Gly Ser Thr Val Asp
                165                 170                 175

His Gln Gly Val Ser Trp Tyr His Trp Lys Gly Phe Glu Phe Ser Val
            180                 185                 190

Pro Phe Thr Glu Met Lys Leu Arg Pro Arg Asn Phe Arg Ser Pro Ala
        195                 200                 205

Gly Gly Gly
    210

<210> SEQ ID NO 36
<211> LENGTH: 782
<212> TYPE: PRT
<213> ORGANISM: Homo sapiens

<400> SEQUENCE: 36

Thr Phe Asp Asn Leu Ser Pro Gly Leu Glu Tyr Asn Val Ser Val Tyr
  1               5                  10                  15

Thr Val Lys Asp Asp Lys Glu Ser Val Pro Ile Ser Asp Thr Ile Ile
             20                  25                  30

Pro Ala Val Pro Pro Pro Thr Asp Leu Arg Phe Thr Asn Ile Gly Pro
             35                  40                  45

Asp Thr Met Arg Val Thr Trp Ala Pro Pro Ser Ile Asp Leu Thr
 50                  55                  60

Asn Phe Leu Val Arg Tyr Ser Pro Val Lys Asn Glu Glu Asp Val Ala
 65                  70                  75                  80

Glu Leu Ser Ile Ser Pro Ser Asp Asn Ala Val Val Leu Thr Asn Leu
                 85                  90                  95

Leu Pro Gly Thr Glu Tyr Val Val Ser Val Ser Ser Val Tyr Glu Gln
                100                 105                 110

His Glu Ser Thr Pro Leu Arg Gly Arg Gln Lys Thr Gly Leu Asp Ser
            115                 120                 125

Pro Thr Gly Ile Asp Phe Ser Asp Ile Thr Ala Asn Ser Phe Thr Val
        130                 135                 140

His Trp Ile Ala Pro Arg Ala Thr Ile Thr Gly Tyr Arg Ile Arg His
145                 150                 155                 160

His Pro Glu His Phe Ser Gly Arg Pro Arg Glu Asp Arg Val Pro His
                165                 170                 175

Ser Arg Asn Ser Ile Thr Leu Thr Asn Leu Thr Pro Gly Thr Glu Tyr
            180                 185                 190

Val Val Ser Ile Val Ala Leu Asn Gly Arg Glu Glu Ser Pro Leu Leu
        195                 200                 205

```
Ile Gly Gln Gln Ser Thr Val Ser Asp Val Pro Arg Asp Leu Glu Val
210                 215                 220

Val Ala Ala Thr Pro Thr Ser Leu Leu Ile Ser Trp Asp Ala Pro Ala
225                 230                 235                 240

Val Thr Val Arg Tyr Tyr Arg Ile Thr Tyr Gly Glu Thr Gly Gly Asn
            245                 250                 255

Ser Pro Val Gln Glu Phe Thr Val Pro Gly Ser Lys Ser Thr Ala Thr
                260                 265                 270

Ile Ser Gly Leu Lys Pro Gly Val Asp Tyr Thr Ile Thr Val Tyr Ala
            275                 280                 285

Val Thr Gly Arg Gly Asp Ser Pro Ala Ser Ser Lys Pro Ile Ser Ile
290                 295                 300

Asn Tyr Arg Thr Glu Ile Asp Lys Pro Ser Gln Met Gln Val Thr Asp
305                 310                 315                 320

Val Gln Asp Asn Ser Ile Ser Val Lys Trp Leu Pro Ser Ser Ser Pro
                325                 330                 335

Val Thr Gly Tyr Arg Val Thr Thr Thr Pro Lys Asn Gly Pro Gly Pro
            340                 345                 350

Thr Lys Thr Lys Thr Ala Gly Pro Asp Gln Thr Glu Met Thr Ile Glu
            355                 360                 365

Gly Leu Gln Pro Thr Val Glu Tyr Val Val Ser Val Tyr Ala Gln Asn
370                 375                 380

Pro Ser Gly Glu Ser Gln Pro Leu Val Gln Thr Ala Val Thr Thr Ile
385                 390                 395                 400

Pro Ala Pro Thr Asp Leu Lys Phe Thr Gln Val Thr Pro Thr Ser Leu
                405                 410                 415

Ser Ala Gln Trp Thr Pro Pro Asn Val Gln Leu Thr Gly Tyr Arg Val
                420                 425                 430

Arg Val Thr Pro Lys Glu Lys Thr Gly Pro Met Lys Glu Ile Asn Leu
            435                 440                 445

Ala Pro Asp Ser Ser Ser Val Val Val Ser Gly Leu Met Val Ala Thr
450                 455                 460

Lys Tyr Glu Val Ser Val Tyr Ala Leu Lys Asp Thr Leu Thr Ser Arg
465                 470                 475                 480

Pro Ala Gln Gly Val Val Thr Thr Leu Glu Asn Val Ser Pro Pro Arg
                485                 490                 495

Arg Ala Arg Val Thr Asp Ala Thr Glu Thr Thr Ile Thr Ile Ser Trp
            500                 505                 510

Arg Thr Lys Thr Glu Thr Ile Thr Gly Phe Gln Val Asp Ala Val Pro
            515                 520                 525

Ala Asn Gly Gln Thr Pro Ile Gln Arg Thr Ile Lys Pro Asp Val Arg
            530                 535                 540

Ser Tyr Thr Ile Thr Gly Leu Gln Pro Gly Thr Asp Tyr Lys Ile Tyr
545                 550                 555                 560

Leu Tyr Thr Leu Asn Asp Asn Ala Arg Ser Ser Pro Val Val Ile Asp
                565                 570                 575

Ala Ser Thr Ala Ile Asp Ala Pro Ser Asn Leu Arg Phe Leu Ala Thr
            580                 585                 590

Thr Pro Asn Ser Leu Leu Val Ser Trp Gln Pro Pro Arg Ala Arg Ile
            595                 600                 605

Thr Gly Tyr Ile Ile Lys Tyr Glu Lys Pro Gly Ser Pro Pro Arg Glu
610                 615                 620
```

```
Val Val Pro Arg Pro Arg Pro Gly Val Thr Glu Ala Thr Ile Thr Gly
625                 630                 635                 640

Leu Glu Pro Gly Thr Glu Tyr Thr Ile Tyr Val Ile Ala Leu Lys Asn
            645                 650                 655

Asn Gln Lys Ser Glu Pro Leu Ile Gly Arg Lys Lys Thr Val Gln Lys
        660                 665                 670

Thr Pro Phe Val Thr His Pro Gly Tyr Asp Thr Gly Asn Gly Ile Gln
        675                 680                 685

Leu Pro Gly Thr Ser Gly Gln Gln Pro Ser Val Gln Gln Met Ile
    690                 695                 700

Phe Glu Glu His Gly Phe Arg Arg Thr Thr Pro Pro Thr Thr Ala Thr
705                 710                 715                 720

Pro Ile Arg His Arg Pro Arg Pro Tyr Pro Pro Asn Val Gly Gln Glu
                725                 730                 735

Ala Leu Ser Gln Thr Thr Ile Ser Trp Ala Pro Phe Gln Asp Thr Ser
            740                 745                 750

Glu Tyr Ile Ile Ser Cys His Pro Val Gly Thr Asp Glu Glu Pro Leu
            755                 760                 765

Gln Phe Arg Val Pro Gly Thr Ser Thr Ser Ala Thr Leu Thr
770                 775                 780

<210> SEQ ID NO 37
<211> LENGTH: 7
<212> TYPE: PRT
<213> ORGANISM: Artificial Sequence
<220> FEATURE:
<223> OTHER INFORMATION: monoclonal antibody complementarity determining
      region
<220> FEATURE:
<221> NAME/KEY: VARIANT
<222> LOCATION: 2
<223> OTHER INFORMATION: Xaa - Tyr or Phe
<220> FEATURE:
<221> NAME/KEY: VARIANT
<222> LOCATION: 3
<223> OTHER INFORMATION: Xaa = Thr or Ser
<220> FEATURE:
<221> NAME/KEY: VARIANT
<222> LOCATION: 4
<223> OTHER INFORMATION: Xaa = any amino acid

<400> SEQUENCE: 37

Gly Xaa Xaa Xaa Thr Ser Tyr
1               5

<210> SEQ ID NO 38
<211> LENGTH: 10
<212> TYPE: PRT
<213> ORGANISM: Artificial Sequence
<220> FEATURE:
<223> OTHER INFORMATION: monoclonal antibody complementarity determining
      region
<220> FEATURE:
<221> NAME/KEY: VARIANT
<222> LOCATION: 2, 3, 4,  7, 8, 9
<223> OTHER INFORMATION: Xaa = any amino acid

<400> SEQUENCE: 38

Gly Xaa Xaa Xaa Tyr Asn Xaa Xaa Xaa Lys
1               5                   10

<210> SEQ ID NO 39
<211> LENGTH: 10
<212> TYPE: PRT
<213> ORGANISM: Artificial Sequence
```

```
<220> FEATURE:
<223> OTHER INFORMATION: monoclonal antibody complementarity determining
      region
<220> FEATURE:
<221> NAME/KEY: VARIANT
<222> LOCATION: 2, 3, 4, 5, 6, 8
<223> OTHER INFORMATION: Xaa = any amino acid

<400> SEQUENCE: 39

Tyr Xaa Xaa Xaa Xaa Xaa Ala Xaa Asp Tyr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: monoclonal antibody complementarity determining
      region
<220> FEATURE:
<221> NAME/KEY: VARIANT
<222> LOCATION: 5
<223> OTHER INFORMATION: Xaa = Asp or Asn
<220> FEATURE:
<221> NAME/KEY: VARIANT
<222> LOCATION: 8
<223> OTHER INFORMATION: Xaa = Ser or Thr
<220> FEATURE:
<221> NAME/KEY: VARIANT
<222> LOCATION: 9
<223> OTHER INFORMATION: Xaa = any amino acid

<400> SEQUENCE: 40

Lys Ala Ser Gln Xaa Val Gly Xaa Xaa Val Ala
1               5                   10

<210> SEQ ID NO 41
<211> LENGTH: 6
<212> TYPE: PRT
<213> ORGANISM: Artificial Sequence
<220> FEATURE:
<223> OTHER INFORMATION: monoclonal antibody complementarity determining
      region
<220> FEATURE:
<221> NAME/KEY: VARIANT
<222> LOCATION: 3
<223> OTHER INFORMATION: Xaa = any amino acid

<400> SEQUENCE: 41

Ala Ser Xaa Arg His Thr
1               5

<210> SEQ ID NO 42
<211> LENGTH: 8
<212> TYPE: PRT
<213> ORGANISM: Artificial Sequence
<220> FEATURE:
<223> OTHER INFORMATION: monoclonal antibody complementarity determining
      region
<220> FEATURE:
<221> NAME/KEY: VARIANT
<222> LOCATION: 3, 4
<223> OTHER INFORMATION: Xaa = any amino acid

<400> SEQUENCE: 42

Gln Tyr Xaa Xaa Tyr Pro Leu Thr
1               5
```